US006293750B1

(12) United States Patent
Cohen et al.

(10) Patent No.: US 6,293,750 B1
(45) Date of Patent: *Sep. 25, 2001

(54) ROBOTICS FOR TRANSPORTING CONTAINERS AND OBJECTS WITHIN AN AUTOMATED ANALYTICAL INSTRUMENT AND SERVICE TOOL FOR SERVICING ROBOTICS

(75) Inventors: Beri Cohen, Hartsdale; Thomas W. DeYoung, Stormville; Krunoslav Esteban Draganovic, Upper Nyack; Lev Vant, Rego Park, all of NY (US); Richard S. Antoszewski, Glenshaw, PA (US); Joseph J. Zelezniak, Upper St. Clair, PA (US); Edward R. Sieger, Jr., Pittsburgh, PA (US)

(73) Assignee: Bayer Corporation, Tarrytown, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/534,388

(22) Filed: Mar. 24, 2000

Related U.S. Application Data

(62) Division of application No. 09/115,080, filed on Jul. 14, 1998.

(51) Int. Cl.⁷ .................................................. B66C 23/00
(52) U.S. Cl. .................................. 414/744.4; 414/749.3; 414/751.1; 901/2; 901/17
(58) Field of Search ............................. 414/749.3, 751.1, 414/744.3, 744.2, 744.4; 901/17, 2, 9

(56) References Cited

U.S. PATENT DOCUMENTS 1,909,813 * 5/1933 Crosbie ................................. 294/902

(List continued on next page.)

FOREIGN PATENT DOCUMENTS

3234593 A1    7/1983  (DE) .............................. G01N/35/00

(List continued on next page.)

OTHER PUBLICATIONS

PCT publication No. WO 87/05401 cover sheet with English abstract; specification page 5; drawing sheet 1, Sep. 11, 1987.

(List continued on next page.)

*Primary Examiner*—Robert P. Olszewski
*Assistant Examiner*—Bryan Jaketic
(74) *Attorney, Agent, or Firm*—Andrew L. Klawitter; John M. Paolino

(57) ABSTRACT

A robotic arm has a pair of gripper fingers designed to grip a variety of containers, including capped and uncapped test tubes as well as containers having unique gripping means. The fingers each have upper and lower projections separated by a groove, the respective projections facing each other when mounted to grippers on the robotic arm. The projections and groove serve to firmly hold the containers as well as self-align the unique gripping means on initially unaligned containers within the fingers as the fingers close around the containers. The fingers have clearance to avoid contact with caps on capped test tubes. Stops are provided at the top of each finger to engage one another and prevent fully closed fingers from deforming. The robotic arm may be transported along a rail mounted above the instrument and a gripper assembly, having a gripper arm, mounted to the robotic arm may be rotated above the instrument to move the container to various locations within the instrument. Side posts on the instruments have a gap between them that permits the gripper arm to rotate and extend outwards to interface with an adjacent instrument or a lab automation transport line.

5 Claims, 30 Drawing Sheets

U.S. PATENT DOCUMENTS

| | | | |
|---|---|---|---|
| 3,579,303 | 5/1971 | Pickering | 23/230 |
| 3,741,409 * | 6/1973 | Painter | 901/39 |
| 3,871,832 | 3/1975 | Leblanc | 23/259 |
| 3,976,028 | 8/1976 | Howells et al. | 118/6 |
| 4,298,570 | 11/1981 | Lillig et al. | 422/64 |
| 4,305,130 * | 12/1981 | Kelley et al. | 901/17 |
| 4,311,667 | 1/1982 | Gocho | 422/64 |
| 4,319,864 * | 3/1982 | Kaufeldt | 414/751.1 |
| 4,368,913 * | 1/1983 | Brockmann et al. | 901/39 |
| 4,451,433 | 5/1984 | Yamashita et al. | 422/63 |
| 4,452,899 | 6/1984 | Alston | 436/46 |
| 4,453,807 | 6/1984 | Faulkner et al. | 350/529 |
| 4,501,495 | 2/1985 | Faulkner et al. | 356/244 |
| 4,505,636 * | 3/1985 | Sugino et al. | 901/39 |
| 4,557,154 | 12/1985 | Iwata et al. | 74/89.21 |
| 4,670,219 | 6/1987 | Nelson et al. | 422/63 |
| 4,676,951 | 6/1987 | Armes et al. | 422/65 |
| 4,708,886 | 11/1987 | Nelson | 422/72 |
| 4,723,353 * | 2/1988 | Monforte | 901/39 |
| 4,735,487 | 4/1988 | Thorwirth et al. | 350/162.12 |
| 4,738,824 | 4/1988 | Takeuchi | 422/63 |
| 4,758,409 | 7/1988 | Uffenheimer | 422/102 |
| 4,781,891 | 11/1988 | Galle et al. | 422/64 |
| 4,788,141 | 11/1988 | Yamasaki et al. | 435/18 |
| 4,803,050 | 2/1989 | Mack | 422/65 |
| 4,807,984 | 2/1989 | Kurimura et al. | 350/529 |
| 4,835,707 | 5/1989 | Amano et al. | 364/497 |
| 4,835,711 | 5/1989 | Hutchins et al. | 364/513 |
| 4,837,159 | 6/1989 | Yamada | 436/45 |
| 4,874,250 | 10/1989 | Gonner | 374/43 |
| 4,890,247 | 12/1989 | Sarrine et al. | 364/571.04 |
| 4,909,920 | 3/1990 | Sarrine et al. | 204/299 |
| 4,931,402 | 6/1990 | Abplanalp | 435/291 |
| 4,950,319 | 8/1990 | Lane et al. | 65/12 |
| 4,951,513 | 8/1990 | Koike | 73/864.25 |
| 4,954,237 | 9/1990 | Sarrine et al. | 204/299 |
| 4,955,653 * | 9/1990 | Beals | 901/39 |
| 4,961,915 | 10/1990 | Martin | 422/116 |
| 4,962,041 | 10/1990 | Roginski | 436/150 |
| 4,986,891 | 1/1991 | Sarrine et al. | 204/299 |
| 5,004,582 | 4/1991 | Miyata et al. | 422/56 |
| 5,051,238 | 9/1991 | Umetsu et al. | 422/64 |
| 5,055,408 | 10/1991 | Higo et al. | 436/48 |
| 5,061,639 | 10/1991 | Lung et al. | 436/164 |
| 5,080,864 | 1/1992 | Shaw | 422/62 |
| 5,084,242 | 1/1992 | Sakuma et al. | 422/100 |
| 5,096,828 | 3/1992 | Ishizaka et al. | 436/44 |
| 5,104,621 | 4/1992 | Pfost et al. | 422/67 |
| 5,108,703 | 4/1992 | Pfost et al. | 422/65 |
| 5,125,748 | 6/1992 | Bjornson et al. | 356/414 |
| 5,128,103 | 7/1992 | Wang et al. | 422/64 |
| 5,139,744 | 8/1992 | Kowalski | 422/67 |
| 5,158,895 | 10/1992 | Ashihara et al. | 436/526 |
| 5,166,889 | 11/1992 | Cloyd | 364/510 |
| 5,175,086 | 12/1992 | Takekawa et al. | 435/7.92 |
| 5,183,638 | 2/1993 | Wakatake | 422/64 |
| 5,206,568 | 4/1993 | Bjornson et al. | 318/568.1 |
| 5,260,872 | 11/1993 | Copeland et al. | 364/413.07 |
| 5,277,871 | 1/1994 | Fujii et al. | 422/70 |
| 5,292,482 | 3/1994 | Manabe | 422/64 |
| 5,294,404 | 3/1994 | Grandone et al. | 422/64 |
| 5,324,480 | 6/1994 | Shumate et al. | 422/63 |
| 5,347,914 | 9/1994 | Kinoshita . | |
| 5,358,691 | 10/1994 | Clark et al. | 422/64 |
| 5,366,896 | 11/1994 | Margrey et al. | 436/48 |
| 5,369,566 | 11/1994 | Pfost et al. | 364/147 |
| 5,415,840 | 5/1995 | Sano et al. | 422/67 |
| 5,424,036 | 6/1995 | Ushikubo | 422/64 |
| 5,425,918 | 6/1995 | Healey et al. | 422/64 |
| 5,443,791 | 8/1995 | Cathcart et al. | 422/65 |
| 5,482,863 | 1/1996 | Knobel | 436/54 |
| 5,496,517 | 3/1996 | Pfost et al. | 422/63 |
| 5,628,962 | 5/1997 | Kanbara et al. | 422/63 |
| 5,769,775 | 6/1998 | Quinlan . | |
| 5,813,823 * | 9/1998 | Hofmeister | 414/744.2 |

FOREIGN PATENT DOCUMENTS

| | | | |
|---|---|---|---|
| 8424341.4 U1 | 5/1985 | (DE) | G01N/35/06 |
| 8702984.7 U1 | 9/1987 | (DE) | G01N/35/02 |
| 3801218 A1 | 8/1988 | (DE) | G01N/1/02 |
| 4004198 A1 | 8/1991 | (DE) | G05D/7/00 |
| 4110380 A1 | 10/1991 | (DE) | G01N/35/02 |
| 3621586 A1 | 4/1992 | (DE) | G01N/35/00 |
| 3621586 C2 | 4/1992 | (DE) | G01N/35/00 |
| 4203574 A1 | 8/1992 | (DE) | G01N/35/02 |
| 4118886 | 12/1992 | (DE) | G01N/35/02 |
| 9207767.6 U1 | 7/1993 | (DE) | G01N/35/02 |
| 29608120 U1 | 9/1996 | (DE) | B01L/11/00 |
| 0 251 044 A2 | 1/1988 | (EP) | C08L/51/04 |
| 0 258 565 A2 | 3/1988 | (EP) | G01N/1/00 |
| 0 285 116 A2 | 10/1988 | (EP) | A61L/2/24 |
| 0 703 455 A1 | 3/1996 | (EP) | G01N/35/00 |
| 2 200 469 A | 8/1988 | (GB) | G01G/19/38 |
| 0140155 | 11/1980 | (JP) | G01N/35/06 |
| 0090162 | 6/1982 | (JP) | G01N/35/02 |
| 0040234 | 3/1984 | (JP) | G01N/1/100 |
| 61189457 | 8/1986 | (JP) . | |
| 1195362 | 8/1989 | (JP) | G01N/30/18 |
| 403012554 | 1/1991 | (JP) | G01N/35/04 |
| 403186763 | 8/1991 | (JP) | G01N/35/04 |
| 40419168 | 7/1992 | (JP) | G01N/33/493 |
| 404335159 | 11/1992 | (JP) | G01N/35/04 |
| WO 90/03834 | 4/1990 | (WO) | B01D/45/12 |
| WO 91/16675 | 10/1991 | (WO) | G01N/21/01 |
| WO 91/17445 | 11/1991 | (WO) | G01N/35/06 |
| WO 93/15407 | 8/1993 | (WO) | G01N/35/00 |
| WO 9315407 | 8/1993 | (WO) . | |
| WO 9506545 | 3/1995 | (WO) . | |
| WO 95/33240 | 12/1995 | (WO) | G06F/15/46 |

OTHER PUBLICATIONS

PCT publication No. WO 93/20612 cover sheet with English abstract; specification pp. 24–26; drawing sheets 1–14, Oct. 14, 1993.

PCT publication No. WO 93/21534 cover sheet with English abstract; specification p. 16, drawing sheets 1–4, Oct. 28, 1993.

PCT publication No. WO 94/14073 cover sheet; specification p. 14, drawings sheets 1–12, Jun. 23, 1994.

European publication No. 0 753 745 A2 cover sheet with English abstract and Fig. 1, Jan. 15, 1997.

European publication No. 0 745 855 A2 cover sheet; page 19 of specification (claims 1–10); Fig 1, Dec. 4, 1996.

European publication No. 0 732 591 A2 cover sheet; Fig. 12, Sep. 18, 1996.

European publication No. 0 731 355 A2 cover sheet; specification p. 6; Fig. 1, Sep. 11, 1996.

European publication No. 0 672 906 A1 cover sheet; specification columns 21–24; Figs. 1–3, Sep. 20, 1995.

European publication No. 0 658 769 A1 cover sheet; Fig. 1, Jun. 21, 1995.

European publication No. 0 608 425 A1 cover sheet; specification p. 6; Figs 1 and 3, Aug. 3, 1994.

European publication No. 0 590 730 A2 cover sheet; Fig. 1, Apr. 6, 1994.

European publication No. 0 559 558 A1 abstract Sep. 8, 1993.

European publication No. 0 555 710 A2 cover sheet (in German); Figs. 1–2, Aug. 18, 1993.
European publication No. 0 502 638 A2 cover sheet with English abstract, Sep. 9, 1992.
European publication No. 0 474 145 A2 cover sheet; specification p. 7; Fig 1, Mar. 11, 1992.
European publication No. 0 467 471 A2 cover sheet; Figs. 6a, 6b, 8, Jan. 22, 1992.
European publication No. 0 458 138 A2 cover sheet, Nov. 27, 1991.
European publication No. 0 445 616 A2 cover sheet; specification p. 10, Sep. 11, 1991.
European publication No. 0 438 883 B1 cover sheet; Fig 4, Jul. 31, 1991.
European publication No. 0 411 620 A2 cover sheet; specification p. 13, Feb. 6, 1991.
European publication No. 0 433 462 A1 cover sheet; specification p. 12, Jun. 26, 1991.
European publication No. 0 391 746 A2 cover sheet; Figs. 3 and 4, Oct. 10, 1990.
European publication No. 0 408 804 A2 cover sheet(in German); Fig 1, Jan. 23, 1991.
European publication No. 0 282 076 A2 cover sheet; specification p. 7; Figs. 12 and 13, Mar. 11, 1988.
European publication No. 0 285 215 B1 cover sheet; specification p. 3; Fig. 1; and version A1 cover sheet, Jun. 2, 1993.
European publication No. 0 285 851 B1 cover hseet; specification p. 5; Figs. 1 and 2, Dec. 2, 1992.
European publication No. 0 287 005 A2 cover sheet; specification p. 6; Oct. 19, 1988.
European publication No. 0 299 521 A2 cover sheet; specification p. 19; Fig. 1, Jan. 18, 1989.
European publication No. 0 317 325 A2 cover sheet; specification p. 5; Figs. 1,2, May 24, 1989.
European publication No. 0 355 791 A2 cover sheet; Figs. 1 and 2, Feb. 28, 1990.
European publication No. 0 359 049 A2 cover sheet; specification p. 6, May 21, 1990.
European publication No. 0 377 504 A2 cover sheet; specification p. 4; Jul. 11, 1990.
European publication No. 0 377 505 A2 cover sheet; specification p. 4; Figs. 4 and 5, Jul. 11, 1990.
European publication No. 0 381 308 A1 cover sheet; specification p. 6; Figs. 4,7,8, Aug. 8, 1990.
European publication No. 0 388 018 A2 cover sheet, Sep. 19, 1990.
European publication No. 0 042 340 B1 cover sheet; specification p. 6; drawing sheets 2 and 4, Feb. 13, 1985.
European publication No. 0 042 337 A1 cover sheet, Dec. 23, 1981.
European publication No. 0 046 087 B1 cover sheet; specification p. 7; drawing sheet 1, Apr. 2, 1986.
European publication No. 0 052 006 B1 cover sheet; drawings sheets 1 and 2, May 9, 1982.
European publication No. 0 056 316 B1 cover sheet; specification p. 5; Fig. 1, Oct. 29, 1986.
European publication No. 0 062 251 A1 cover sheet; drawing sheet 6, Oct. 13, 1982.
European publication No. 0 151 375 A2 cover sheet; specification p. 16; drawing sheet 2, Aug. 14, 1985.
European publication No. 0 151 375 B1 cover sheet; specification p. 7; Fig. 3, Oct. 24, 1990.
European publication No. 0 180 792 B1 cover sheet; Fig. 1, Mar. 28, 1990.
European publication No. 0 187 699 A2 cover sheet; specification p. 15; Fig. 1, Jul. 16, 1986.
European publication No. 0 193 385 A2 cover sheet; specification p. 28; Figs. 1 and 3, Sep. 3, 1986.
European publication No. 0 199 466 B1 cover sheet; specification p. 5; Fig. 1, Aug. 22, 1990.
European publication No. 0 223 002 A2 cover sheet; specification p. 10–11; Figs. 1 and 6, May 27, 1987.
European publication No. 0 223 758 B1 cover sheet; Fig. 1, Aug. 28, 1991.
European publication No. 0 255 026 A2 cover sheet; specification p. 51; drawing sheets 1, 2, 5, 7, 14 (of 26), Feb. 3, 1988.
European publication No. 0 571 035 A1 cover sheet, Nov. 24, 1993.
European publication No. 0 594 108 A1 cover sheet; specification pp. 10–11; Fig. 1, Apr. 27, 1994.
European publication No. 0 602 802 A1 cover sheet, Jun. 22, 1994.
German publication No. DE 2448588 C2 cover sheet; specification columns 1–2; Fig. 2, Jan. 30, 1986.
German publication No. DT 2647415 A1 cover sheet; one page of specification; Figs 1–2, May 26, 1977.
German publication No. DE 3102774 C2 cover sheet; specification columns 15–16; Figs. 1 and 3, Jul. 2, 1992.
German publication No. DE 3124948 C2 cover sheet; specification columns 7–8; Fig. 1, May 5, 1992.
German publication No. DE 3143055 C2 cover sheet; specification columns 1–2; Fig. 3, Sep. 22, 1983.
German publication No. DE 3222594 A1 cover sheet; specification pp. 1–2; Figs. 1–15, Jan. 5, 1983.
German publication No. DE 3234563 C2 cover sheet; specification columns 1–2; Fig. 1, Aug. 21, 1986.
German publication No. DE3317560 C2 cover sheet; specification columns 1–3; drawing sheet 1, Oct. 10, 1991.
German publication No. DE 3402304 A1 cover sheet, Jul. 26, 1984.
German publication No. DE 3430170 A1 cover sheet; specification p. 1; drawing sheet 7, Feb. 27, 1986.
German publication No. DE 3503475 C2 cover sheet; specification columns 1–2; Fig. 1A, Aug. 6, 1987.
German publication No. DE 3515824 C2 cover sheet; specification columns 7–8; drawing sheets 2 and 4, Feb. 10, 1994.
German publication No. DE 3533157 A1 cover sheet, Apr. 3, 1986.
German publication No. DE 3614961 C1 cover sheet; specification columns 1–2; Fig. 1 Aug. 13, 1987.
German publication No. DE 3705166, Aug. 27, 1987.
German publication No. DE 3712776 C2 cover sheet; specification columns 11–13; Figs. 1–2B, Dec. 17, 1992.
German publication No. DE 3736632 C2 cover sheet; specification columns 23–24; Figs. 1 and 2, Dec. 19, 1996.
German publication No. DE 3839080 A1 cover sheet; specification columns 15–16; drawing sheets 1–11, Jun. 1, 1989.
German publication No. DE 3908725 C2 cover sheet; specification columns 5–8; Fig. 1, May 29, 1991.
German publication No. DE 3927863 A1 cover sheet, Feb. 28, 1991.
German publication No. DE 3935907 A1 cover sheet; specification columns 23–24; Fig. 22, May 3, 1990.
German publication No. DE 3943524 A1 cover sheet, Feb. 28, 1991.
German publication No. DE 4011584 C2 cover sheet; specification columns 7–8; Fig. 6, Apr. 10, 1990.

German publication No. DE 4113377 C2 cover sheet; specification p. 7; Fig. 2, Sep. 2, 1993.
German publication No. DE 4124724 A1 cover sheet; specification columns 9–10; Fig. 3, Mar. 12, 1992.
German publication No. DE 4136217 A1 cover sheet; specification columns 1–2; Figs. 1–5, May 13, 1993.
German publication No. DE 4119680 C2 cover sheet; specification columns 7–9; Fig. 1, Nov. 11, 1993.
German publication No. DE 4203638 A1 cover sheet; specification columns 7–8; Figs. 1 and 2, Aug. 12, 1993.
German publication No. DE 4211003 A1 cover sheet, Oct. 8, 1992.
German publication No. DE 4214430 C2 cover sheet; specification columns 5–7; Fig. 1, Jun. 30, 1994.
German publication No. DE 4214430 A1 cover sheet; specification columns 11–12; Fig. 1, Jun. 30, 1994.
German publication No. DE 4226694 A1 cover sheet; specification columns 9–10; Fig. 3, Feb. 25, 1993.
German publication No. DE 4230719 A1 cover sheet; specification columns 3–4, Mar. 17, 1994.
German publication No. DE 4306332 A1 cover sheet; specification columns 1–3; Figs. 1–3, Aug. 25, 1994.
German publication No. DE 4309978 C1 cover sheet, Jun. 9, 1994.
German publication No. DE 4310607 A1 cover sheet; specification columns 15–16; Fig 10, Oct. 14, 1993.
German publication No. DE 4310169 A1 cover sheet; specification columns 7–10; Fig. 1, Sep. 30, 1993.
German publication No. DE 4312093 A1 cover sheet; specification columns 7–10; Fig. 1, Oct. 14, 1993.
German publication No. DE 4313399 A1 cover sheet Oct. 28, 1993.
German publication No. DE 4322124 A1 and C2 cover sheet; specification columns 11–12; Fig. 1, Nov. 24, 1994.
German publication No. DE 4406256 A1 cover sheet; specification columns 13–16; Fig. 2, Sep. 1, 1994.
"Send in the Robots", *Analytical Chemistry;* Jan. 1, 1990, vol. 62, No. 1, pp. 29–34.

* cited by examiner

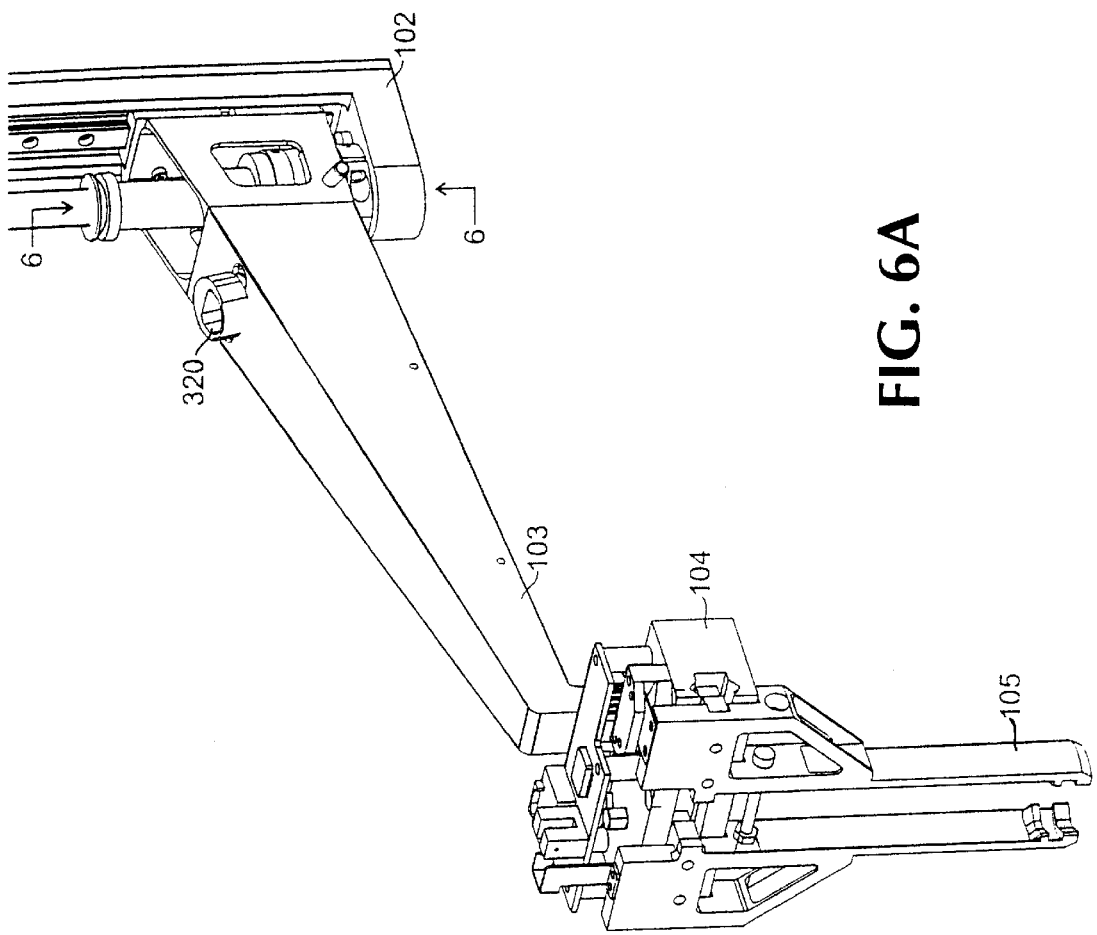

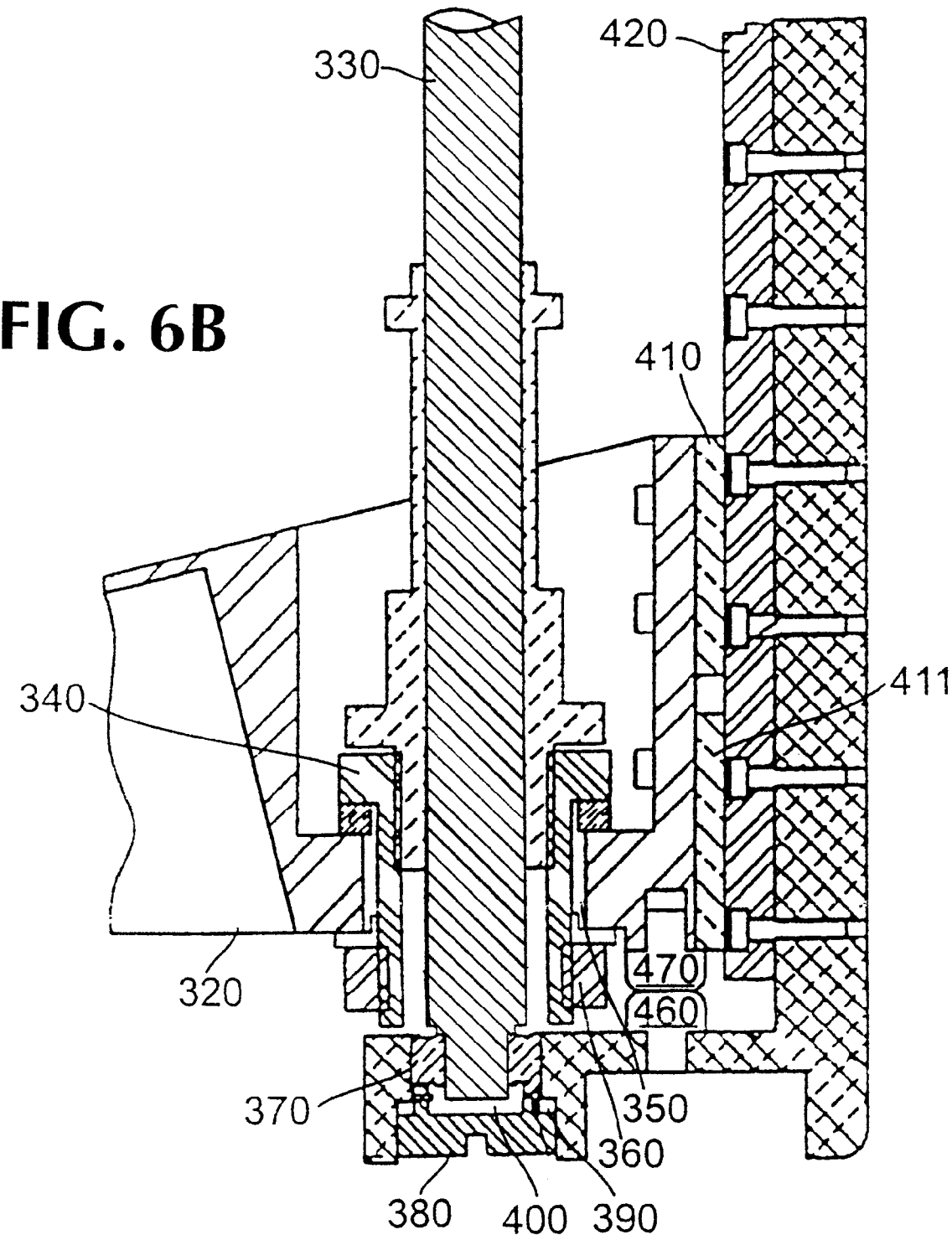

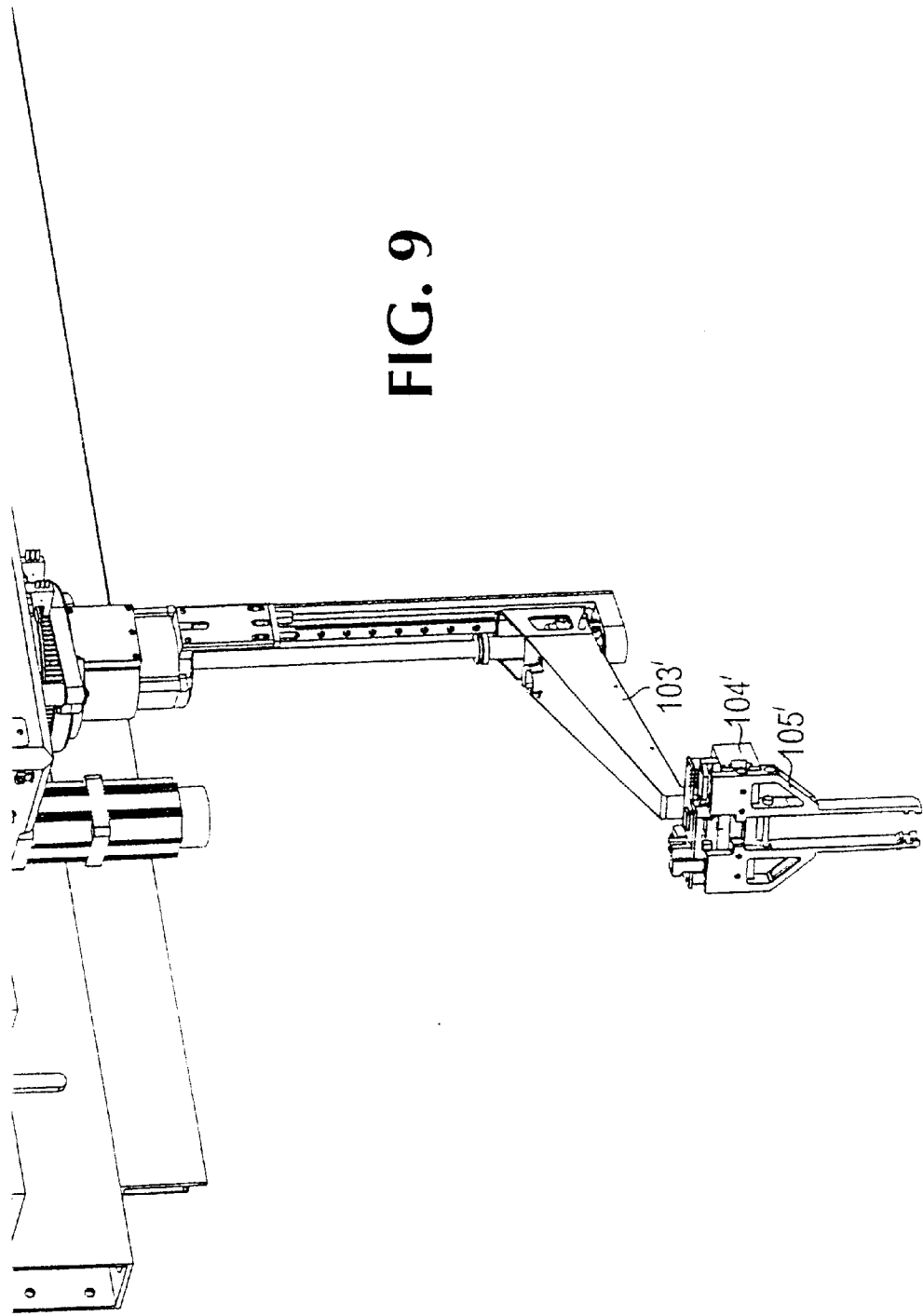

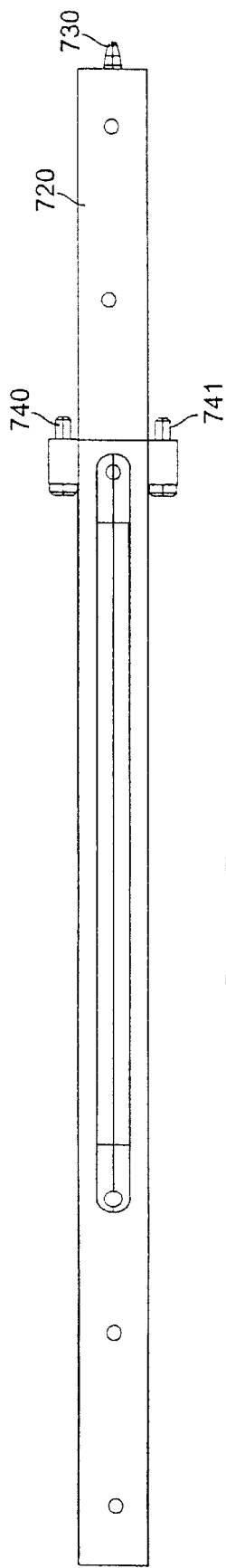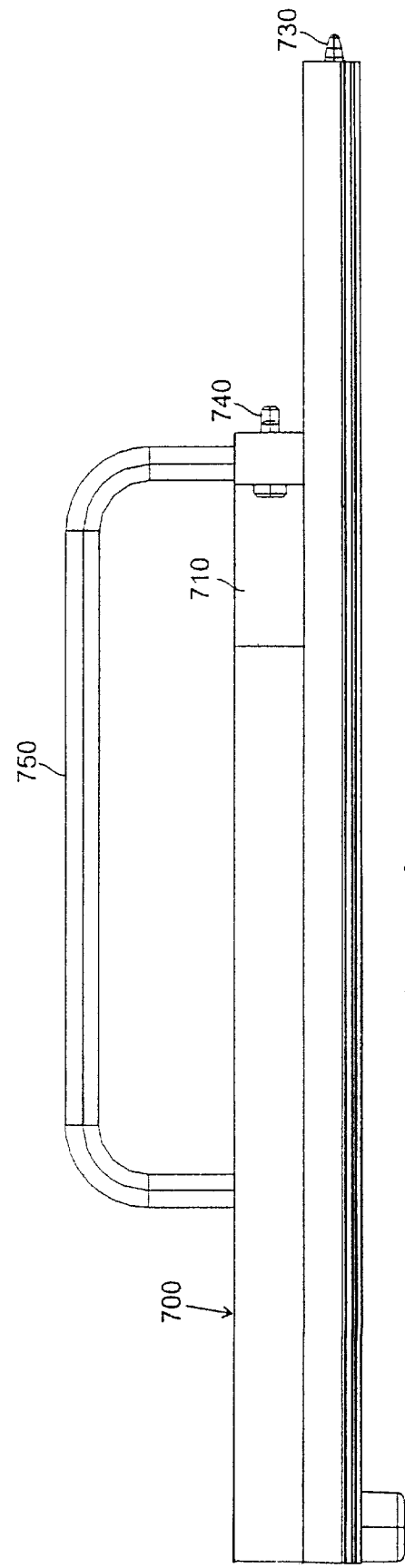

ROBOTICS FOR TRANSPORTING CONTAINERS AND OBJECTS WITHIN AN AUTOMATED ANALYTICAL INSTRUMENT AND SERVICE TOOL FOR SERVICING ROBOTICS

CROSS REFERENCE TO RELATED APPLICATIONS

This application is related to the following U.S. patent applications, having the indicated titles, commonly assigned to the Bayer Corporation of Tarrytown, N.Y. and incorporated by reference herein:

(a) design patent applications for Gripper Finger, Ser. No. 29/090,683, filed concurrently herewith, Sample Tube Rack, Ser. No. 29/090,547, filed Jul. 10, 1998; and Sample Tube Rack, Ser. No. 29/089,359, filed Jun. 15, 1998;

(b) utility patent applications for Sample Tube Rack, Ser. No. 09/113,643, filed Jul. 10, 1998; Sample Tube Rack, Ser. No. 09/097,790, filed Jun. 15, 1998; Reagent Package, Ser. No. 08/985,759, filed Dec. 5, 1997; Diluent Package, Ser. No. 29/088,045, filed May 14, 1998; Automatic Handler for Feeding Containers Into and Out of An Analytical Instrument ("Sample Handler"), Ser. No. 09/115,391, filed concurrently herewith, Automatic Decapper, Ser. No. 09/115,777, filed concurrently herewith; and Cup Handling Subsystem for an Automated Clinical Chemistry Analyzer System, Ser. No. 09/099,739, filed Jun. 18, 1998.

This application is a divisional application of U.S. Ser. No. 09/115,080, filed Jul. 14, 1998.

FIELD OF THE INVENTION

This invention relates to the use of one or more robotic arms in an automated analytical instrument to transport test tubes and other containers or objects between various locations within the instrument and optionally to and from a transport line system in an automated laboratory transport system.

BACKGROUND OF THE INVENTION

Robotics have been incorporated into analytical instruments in various ways. The most common use of robotics in these instruments has been to transport a pipette to aspirate liquid from a test tube. Another use of robotics has been to transport a test tube rack within an automated testing system, as described in U.S. Pat. No. 5,260,872.

Robotics have also been used to transport test tubes within an instrument. For example, U.S. Pat. No. 4,835,711 to Hutchins et al. illustrates a robotic arm transporting a test tube to various work stations which are placed in a circle around the robotic arm. The robotic arm is mounted to a fixed position on the workstation and rotates about an axis perpendicular to the surface of the workstation. As illustrated, the test tube appears to be gripped within gripper fingers, the ends of which are curved in the shape of the test tube. No provision is made to transport containers other than test tubes.

Another robotic arm for transporting a test tube is shown in International Publication No. WO 90/03834. This robotic arm rotates and may lift or lower the test tube but the robotic arm is not translatable along any axis. The gripper fingers are only shown and described as gripping a test tube.

U.S. Pat. No. 4,835,707 to Amano et al. describes a robotic arm that is mounted to the central portion of the workstation and articulates in the x, y, and z axes and rotates in the theta direction. The robot may grasp a sample tube or one of various circular nozzles on the workstation with a chuck.

International Publication No. WO 93/15407 describes the movement of a test tube with a robotic arm with a "hand" to carry the test tube between a mosaic of tesserae of devices and subsidiary devices. The robotic arm may move along a rail in a first axis and a horizontal arm is translatable along second and third axes (vertically and horizontally) and is pivotable about an axis of rotation. This application also teaches that more than one similar apparatuses may be adjoined by and cooperate with another by extending the rails supporting the robots to extend over the adjoining apparatus.

While extending a rail from one apparatus to another similar apparatus is one approach to moving a robotic arm between instruments, this approach is not ideal for transporting objects between more than a few instruments as the rail along which the robotic arm must move becomes significantly long. A better alternative is to use a lab automation transport line to transport test tubes between instruments positioned along the side of the transport line. One such transport line is described in U.S. Pat. No. 5,623,415 to O'Bryan and assigned to SmithKline Beecham Corporation. In the O'Bryan patent, a generic pick-and-place engine, with a robotic arm and grip, is referenced as the means for transferring test tubes between the transport line and the instruments. Alternatively, a pipetting engine may pipette specimens of samples from the test tubes in the transport line for use by the instrument.

SUMMARY OF THE INVENTION

It is an object of this invention to provide one or more robotic arms having gripper fingers that may grip and transport individual containers of various types, including various types and sizes of test tubes (including tubes to hold samples, calibrators and controls), customized reagent and diluent packages, dilution cups and pretreatment incubator covers, from a first, source location to a second, destination location. For simplicity, unless otherwise specified, the term "container" as used in this application shall include, but not be limited to, objects and each of the foregoing specifically enumerated examples of containers. The robotic arm(s) of the present invention may be advantageously used in a variety of applications, such as a means of transport between modules of a modular automated analytical instrument or between an analytical instrument and a sample transport line.

It is a further object of this invention to provide an analytical instrument that may have at least two robotic arms wherein one of the robotic arms is capable of handling the full workload of the instrument if the other robotic arm is disabled.

It is a further object of this invention to provide a robotic arm that has a first attachment for transporting various types of containers from a first location to a second location in an automated analytical instrument and an interchangeable second attachment for transporting the containers from the instrument to a lab automation system or vice versa.

It is a further object of this invention to provide a service tool, which is used to remove robotic arms easily for replacement and service.

It is a further object of this invention to provide a self-teaching process for the robotic arms to account for slight variations in the locations of areas on the instrument which are addressable.

To achieve these objectives, a robotic arm for an analytical instrument has two translational degrees of freedom, a first along the x-axis and a second along the z-axis, and one rotational degree of freedom in a theta direction about the z-axis. The robotic arm comprises a platform that may move along a rail running above the rear of the instrument and defining the x-axis, a lead screw assembly coupled to the platform and defining the z-axis, a gripper arm coupled to the lead screw assembly to move along the lead screw, grippers mounted to the outer end of the gripper arm, and two gripper fingers. The gripper arm, grippers, and gripper fingers may collectively be referred to as the gripper assembly. The x, z and theta movements are powered by respective servo motors and the grippers are coupled to electronics mounted above the grippers, including an inertia switch and an encoder. An analytical instrument may have at least two of these robotic arms to increase the throughput of the instrument and to provide redundancy in the event that one of the robotic arms fail.

In a first aspect of the present invention, each of the gripper fingers on the robotic arm have upper and lower projections separated by a groove. The grooves allows the fingers to grip and transport various types of containers that have flanges that fit within the grooves, including specialized containers, such as reagent and diluent packages and dilution cups designed for use with the instrument, or other containers with flanges. In addition to capturing the flange, the groove self-aligns a misaligned container as the fingers close around the flange by pushing down on the top of the flange with the bottom of the upper projections and pushing up on the bottom of the flange with the top of the lower projections. The fingers may use the upper and lower projections to grip and transport other containers with cylindrical exterior gripping surfaces, including individual test tubes where the fingers are sufficiently long.

In another aspect of the present invention, the distance to which the fingers separate from one another is limited to a distance smaller than the opening of the grippers. This is preferably accomplished with a rod mounted to one of the fingers, passing through an aperture on the other finger, and ending in a stop, which prevents the fingers from separating more than a desired distance.

In another aspect of the present invention, the robotic arm may have an absolute encoder either coupled to the gripper assembly, the platform, or preferably a separate absolute encoder for each of the gripper assembly the platform to determine whether the robotic arm is in a position where it may be safely homed without hitting an obstruction.

In another aspect of the present invention, because it is desirable in certain situations for the reach of the robotic arm not to extend to some areas of the chassis, the robotic arm may instead reach these locations by inserting a container into or removing a container from a shuttle on the chassis that moves along the y-axis and provides access to at least some of those locations to which the robotic arm cannot reach. The shuttle is preferably a rack that may hold multiple containers.

In another aspect of the present invention, the analytical instrument is designed to be used in conjunction with a laboratory automation system. The instrument has side posts and a gap between the side posts that is large enough to allow the gripper arm to pivot outside of the instrument with a sufficient reach for the fingers to transport test tubes between the transport line of the laboratory automation system and the instrument.

In another aspect of the invention, the platform of the robotic arm is coupled to the rail on the instrument with a bearing plate to simplify the removal of the robotic arm for service or replacement. The service or replacement may be further simplified, in yet another aspect of the invention, with a service tool that is mounted to one side of the instrument. The robotic arm may be transferred from the rail on the instrument to a rail extension on the service tool for easier access.

BRIEF DESCRIPTION OF THE DRAWINGS

The inventions and modifications thereof will become better evident from the detailed description below in conjunction with the following figures, in which like reference characters refer to like elements, and in which:

FIG. 6A is a perspective view of the robotic arm with the arm in a fully lowered position along the z-axis;

FIG. 6B is a cross-sectional view of the portion of the robotic arm shown in FIG. 6A along line 6—6;

FIG. 9 is a perspective view of the robotic arm having a gripper arm according to a second embodiment of the invention;

FIG. 17A is a front view of the service tool for the robotic arm; and

FIG. 17B is a bottom view of the service tool of FIG. 17A.

DETAILED DESCRIPTION OF THE PREFERRED EMBODIMENT

Figure 1:
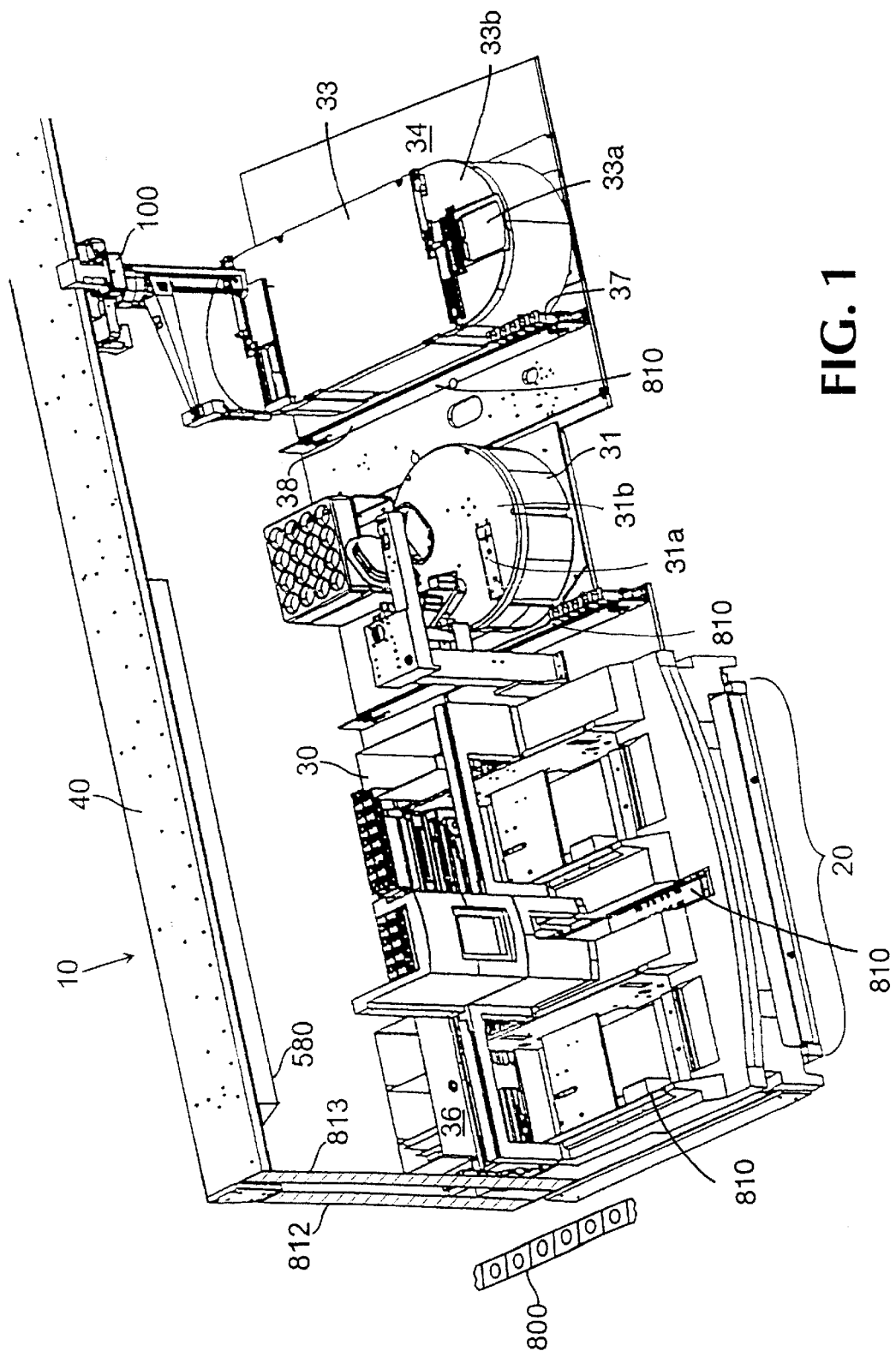
FIG. 1 is an isometric view of a first embodiment of a single robotic arm of the present invention mounted to a beam, which is positioned over various modules of an analytical instrument, and adjacent to a transport system of a laboratory automation system.

Referring to FIG. 1, an analytical instrument 10 has a sample handler module 20 for feeding test tubes of various sizes and other containers to the instrument 10, and one or more additional modules, at least some of which may be optional. The modules prepare a supplied test tube for analysis, if necessary, and then perform one or more analyses on the test tube. Sample handler 20 may include an automatic decapper, as described in the referenced Automatic Decapper application, (not shown in FIG. 1 but which may be located in location 30) for decapping capped test tubes and a reagent activator 36 for preparing reagent packages for use by analytical modules. There may also be a module 31 for processing the tubes before analysis, including a predilution apparatus for adding reagents and diluents to and incubating samples (as described in the referenced "Cup Handling Subsystem" application, and an ion selective electrode apparatus for measuring electrolytes in body fluid. There may also be one or more analytical modules including a clinical analysis module 33, and an immunoassay module represented by box 34. Containers that are transported within the instrument include various types and sizes of capped or uncapped test tubes (including tubes, with or without insert cups, to hold samples, calibrators, and controls), customized reagent and diluent packages, dilution cups and pretreatment incubator covers (which cover the dilution cups in the heated dilution module during the dilution process to confine the heat).

A beam 40 runs above the rear of the instrument 10. (FIG. 2) The length of beam 40 will vary depending on the length of the instrument 10, which may have a varying number of modules. A robotic arm 100, which reaches over at least a rear area of instrument 10, and which for safety reasons is preferably not accessible to the operator, is mounted to beam 40 and is designed for picking up and transporting the containers. Robotic arm 100 comprises several sections, including saddle platform 101, a vertically mounted lead screw assembly 102, a gripper arm 103 coupled to lead screw assembly 102 on one end, and a gripper actuator 104 and gripper fingers 105, including right finger 105$_R$ and left finger 105$_L$, mounted to the other end of gripper arm 103 for gripping the containers.

Robotic arm 100 has four degrees of freedom of movement above the sample handler 20 and modules 30–34. First, the entire robotic arm 100 may move linearly in the direction defined by beam 40 along saddle platform 101. Second, gripper arm 103 may also move linearly up and down along the z-axis defined by lead screw assembly 102. Third, lead screw assembly 102 is rotatable, thereby causing an angular (or theta) motion of gripper arm 103 about the z-axis in a theta direction. Fourth, gripper fingers 105 open and close linearly.

Figure 3A:
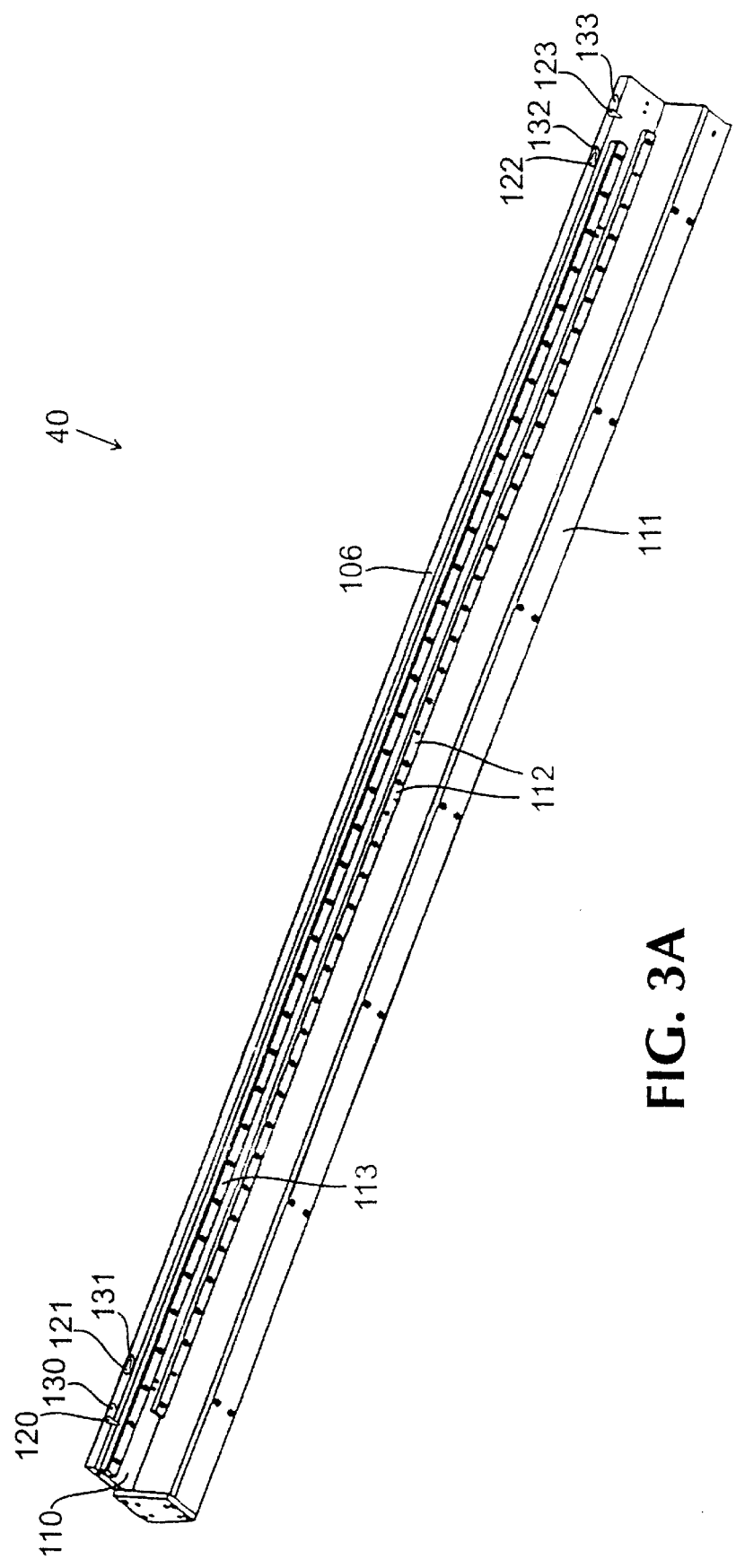
FIG. 3A is an isometric view of the beam including the rail and rack along which the robotic arm moves in the x-direction.

As shown in FIG. 3A, beam 40 comprises a precision plate 110, a beam box assembly 111 mounted to the bottom rear of precision plate 110, a rack 112 mounted to the bottom of precision plate 110 in front of beam box assembly 111, and a linear sliding rail 113 mounted to the bottom of precision plate 110 in front of rack 112. The length of beam 40, rack 112 and rail 113 will depend on the number and size of analytical modules in instrument 10.

Figure 3B:
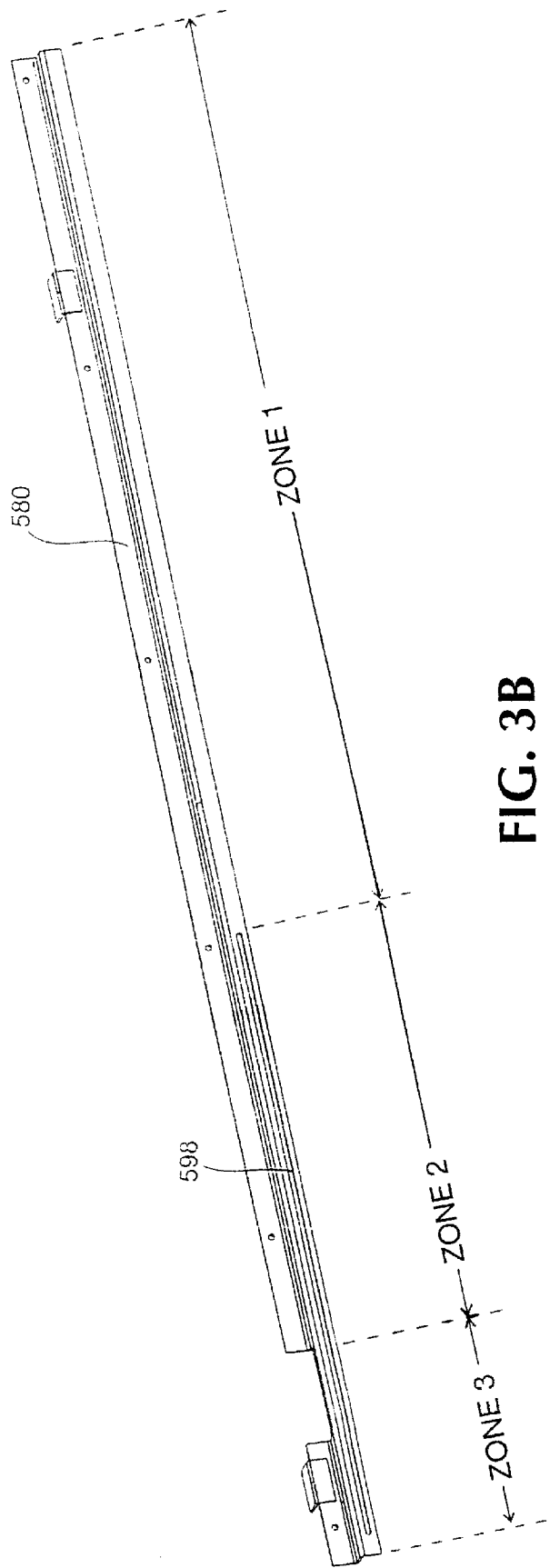
FIG. 3B is a perspective view of the zonal homing bar.

Rotatable hard stops 120–123 are mounted across the top front of beam 40, two near each end of beam 40. Hard stops 120–123 may be rotated upward and into respective exposed recesses 130–133 on the front of beam 40 or may be turned down as shown. Also mounted to the front of beam 40 across the top left side of beam 40 is a zonal homing bar (FIGS. 1 and 3B). The function of hard stops 120–123 and zonal homing bar 580 will be discussed in more detail below.

Robotic arm 100 is mounted to beam 40 with one or more bearing blocks. In the preferred embodiment, the bearing blocks may comprise two linear ball retained bearing blocks 150, 151 coupled the top of saddle platform 101 that are mounted to and linked together by bearing plate 154. (FIGS. 4A and 4B) Bearing blocks 150, 151 may be purchased premounted by the manufacturer to rail 113. While rail 113 may vary in length, preferred rails with premounted bearing blocks are manufactured by IKO of Japan as the LWE series. (For example, for a rail that is 1660 mm long, the preferred rail with bearing blocks is IKO model number LWESC20C2R1660H.) A tongue 152 on each of bearing blocks 150, 151 slides along tracks 153$a$, 153$b$ on the front and back of rail 113. Alternatively, roller bearings may be used to couple robotic arm 100 to rail 113, instead of ball bearings. In determining the number and type of bearing blocks to use, one must take into account that the bearing block or blocks must carry the maximum load of robotic arm 100 loaded with the heaviest container it may carry, and must be able to accelerate and travel at the desired speeds smoothly while keeping noise to a minimum, minimizing torque about each of the x, y and z axes to maintain robotic arm 100 relative to the predefined locations on instrument 10 which it must reach, and not wearing excessively. The maximum torque of each of bearing blocks 150, 151 may be determined from handbooks obtainable from the bearing block manufacturer. Saddle platform 101 is removably mounted to bearing plate 154 to easily remove robotic arm 100 at saddle 101 for service.

Figure 4A:
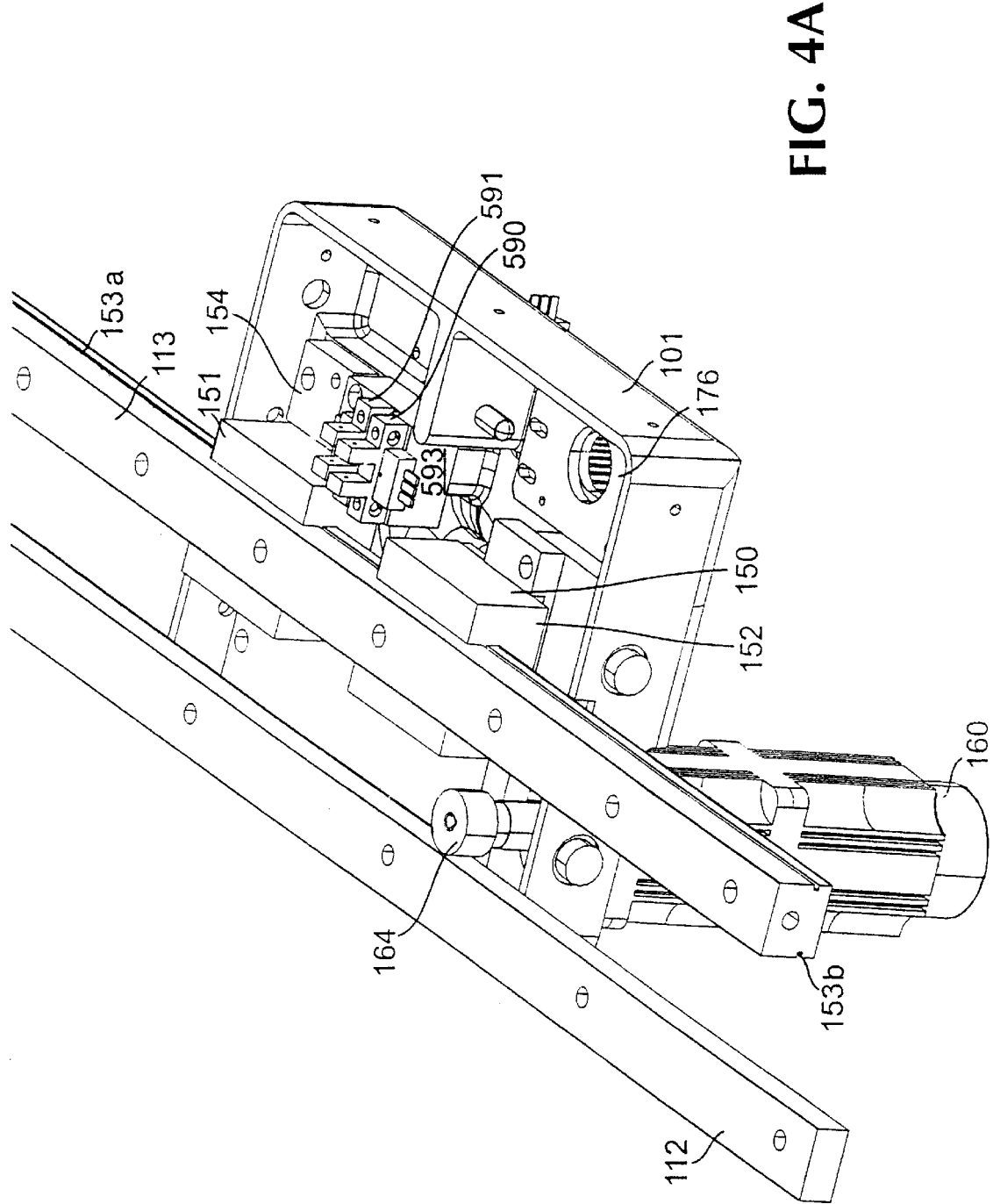
FIG. 4A is an isometric view of the top of the saddle platform mounted to the rail and coupled to the rack (the remainder of the beam and robotic arm are not shown)
Figure 4B:
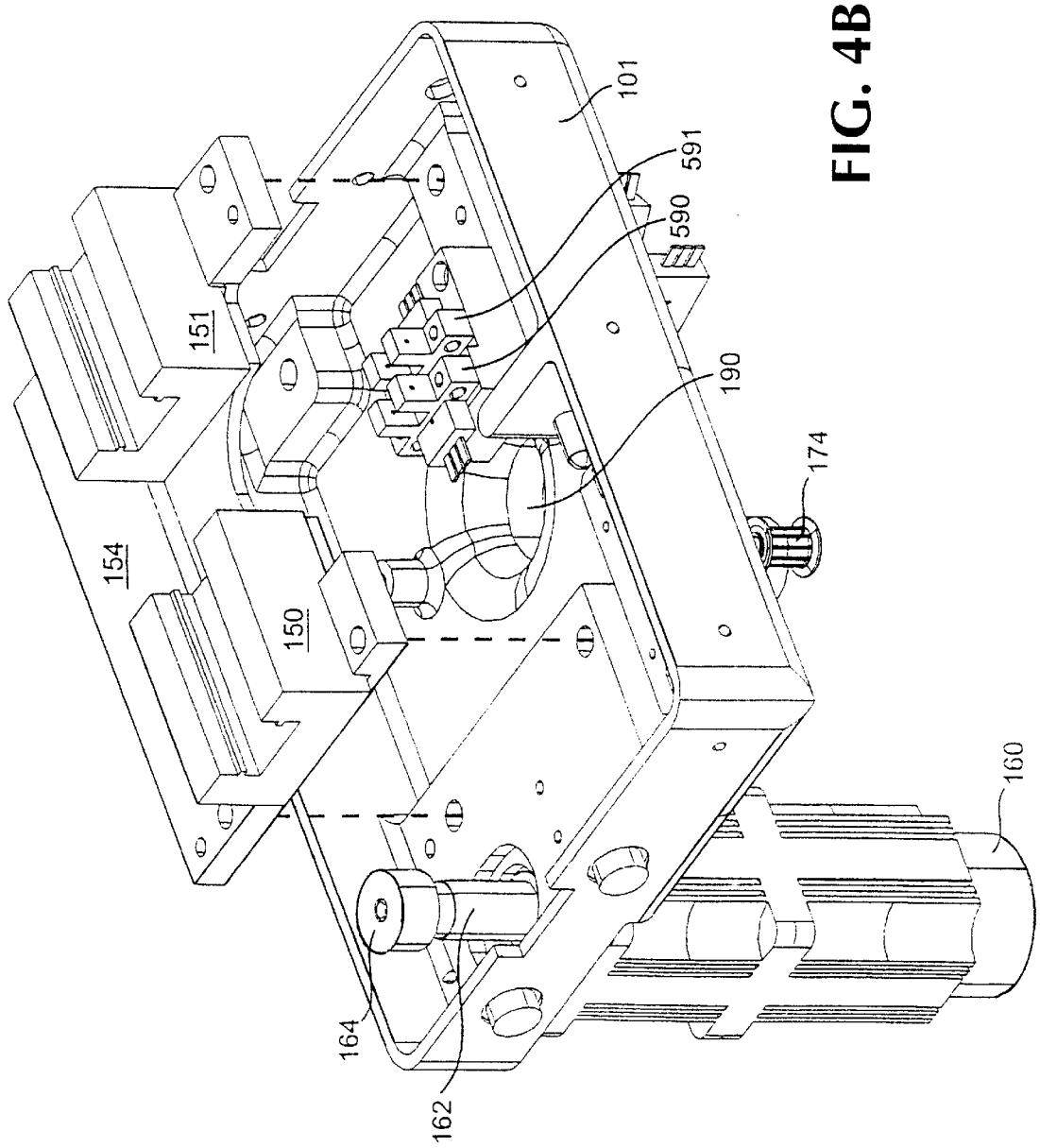
FIG. 4B is an exploded view of the top of the saddle platform separated from the bearing plate.
Figure 5A:
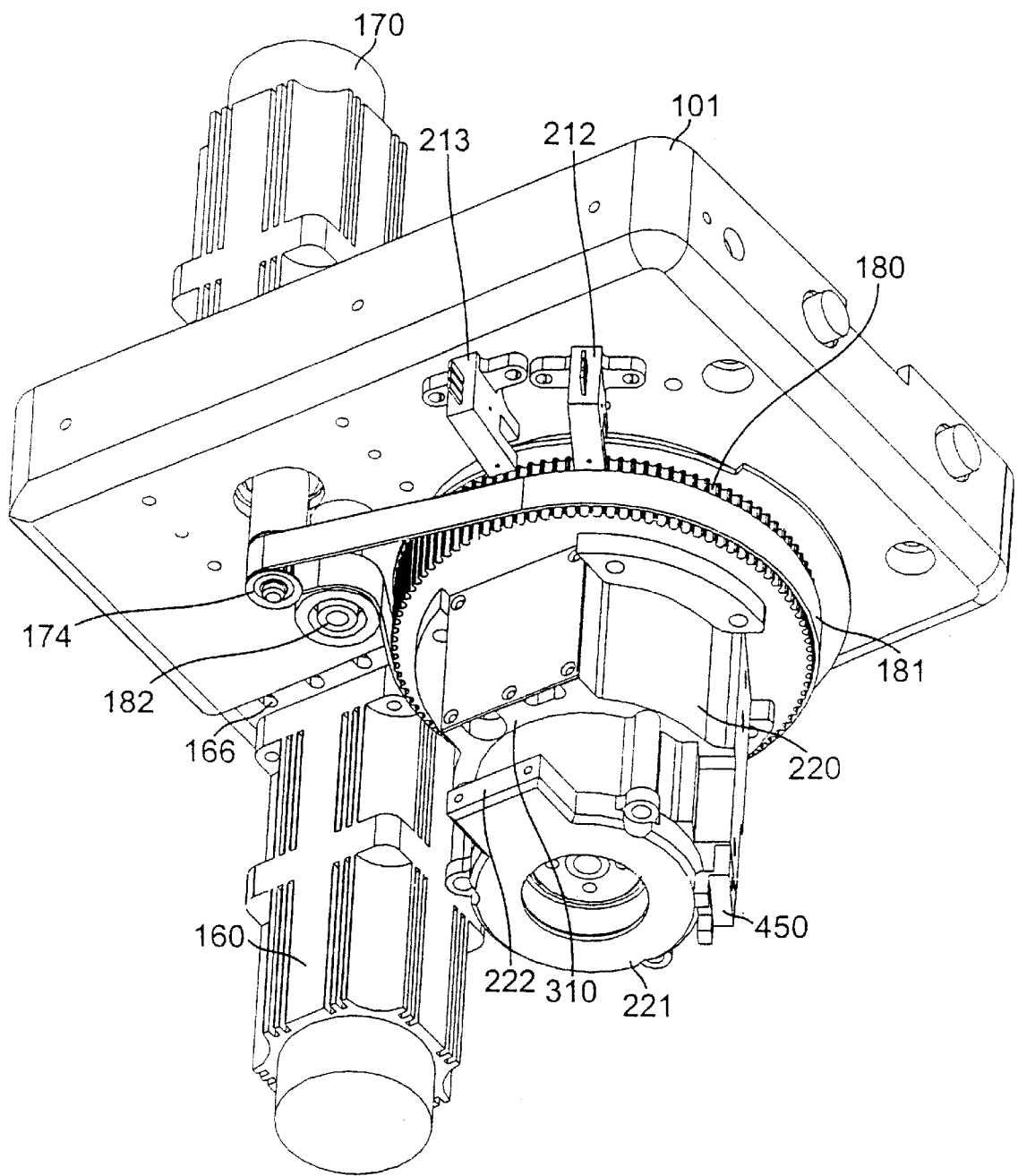
FIG. 5A is an isometric view of the bottom of the saddle platform and the thetamotor and z-motor assemblies (the lead screw assembly is not shown)
Figure 5B:
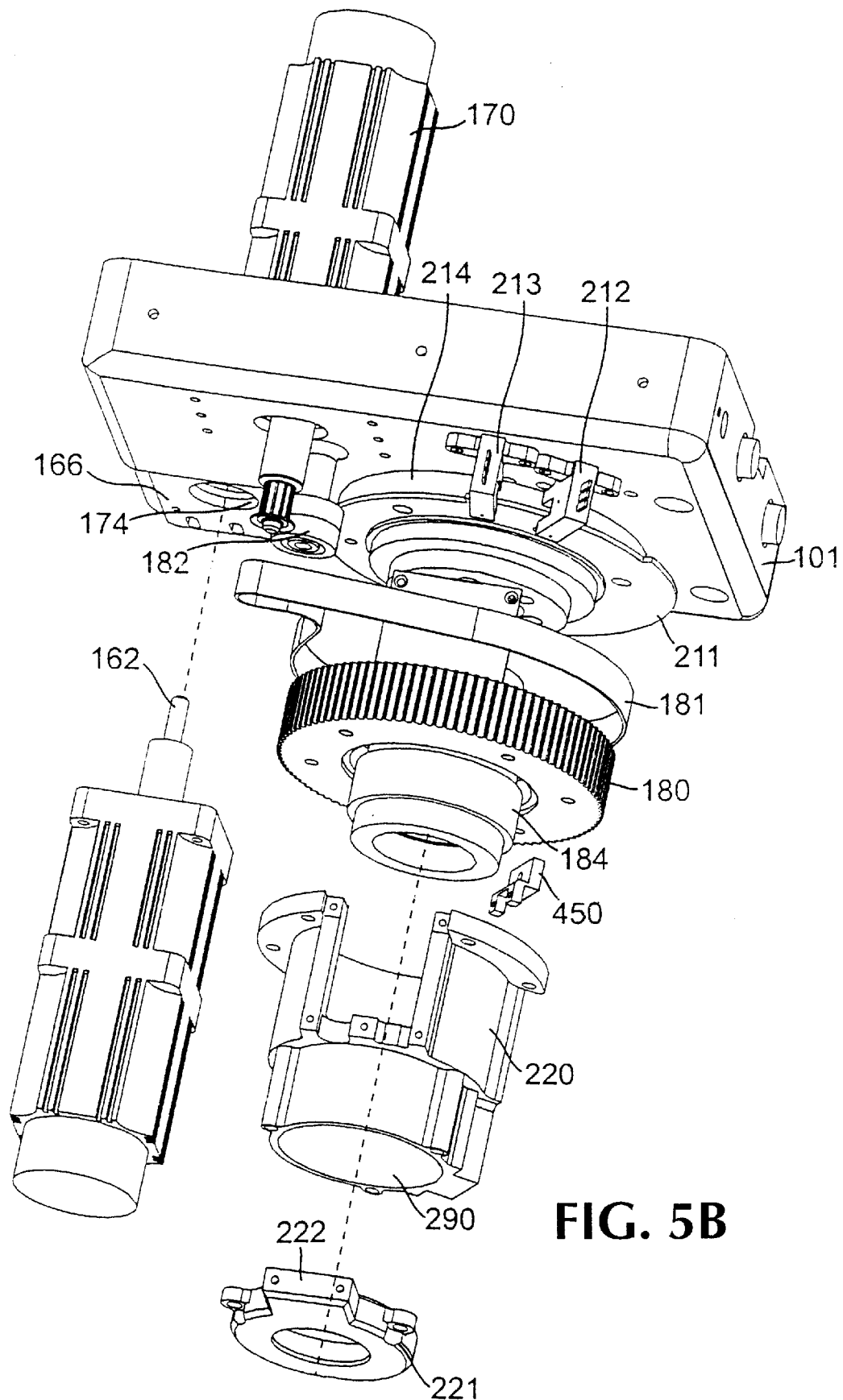
FIGS. 5B and 5C are exploded views of the bottom of the saddle platform shown in FIG. 5A.

Referring to FIGS. 4A and 5B, robotic arm 100 is driven in a linear motion along the x-axis by an "x-motor" 160 mounted beneath saddle platform 101. X-motor 160 is preferably a brushless closed-loop servo motor coupled to a gear box and has a built-in incremental encoder to track the position of robotic arm 100 along rail 113. X-motor 160 may be the motor manufactured by Parker/Compumotor of Rhonert Park, Calif. as Model No. CM160XE-00438 that has a built-in optical encoder to track the position of robotic arm 100 and has a gear box with a gear ratio between the motor and gear of 5.5:1. The particular motor 160 is selected to achieve the desired speeds and accelerations, to prevent oscillations of the robotic arm and to provide smooth transitions when accelerating and decelerating to minimize jerk, which may cause samples in open test tubes to spill and may cause excessive noise. A drive shaft 162 on x-motor 160 passes through saddle platform 101 and attaches to a pinion 164 above saddle platform 101. Pinion 164 engages against rack 112, thereby driving robotic arm 100 in the x-direction. X-motor 160 is mounted to an adjustable mounting plate 166 (FIG. 5C) and mounting plate 166 is mounted to saddle platform 101. Slots 167 on mounting plate 166 allow for the minor adjustment of x-motor toward or away from rack 112 to accommodate some imprecision in the mounting of rack 112 along beam 40. Pinion 164 is held in place with a split hub clamp (not shown).

Figure 4C:
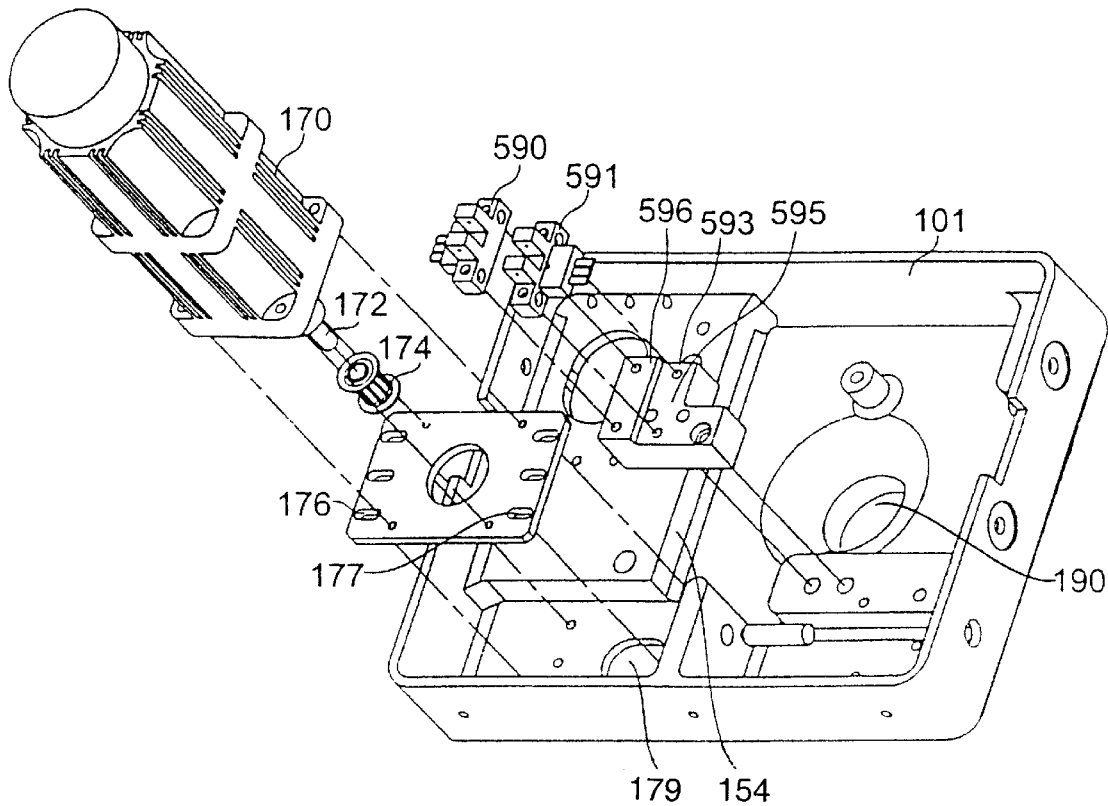
FIG. 4C is a further exploded view of the saddle platform without the bearing plate.

A "theta motor" 170 to rotate gripper arm 103 in a theta direction is mounted to a mounting plate 176 and mounting plate 176 is then mounted to the top of saddle platform 101. (FIG. 4C). Slots 177 in mounting plate 176 provide for the minor adjustment in the positioning of theta motor 170. A drive shaft 172 of theta motor 170 passes through a hole 179 in the bottom of saddle platform 101 and a pulley 174 is attached at the end of drive shaft 172. Pulley 174 is indirectly coupled to a planetary gear 180 mounted underneath saddle platform 101 with a synchronous timing drive belt 181 having teeth. (FIGS. 5A–5C) Drive belt 181 is tightened in place with idler point 182 attached to a mounting pin 183 on the bottom of saddle platform 101 that increases the length of drive belt 181 which contacts pinion 174 and planetary gear 180 and provides for the proper tensioning of drive belt 181. Planetary gear 180 is held in place with a thrust plate 184. A preferred theta motor 170 may be identical to x-motor 160. The drive ratio between planetary gear 180 and pulley 174 for theta motor 170 should preferably be 10:1.

Figure 5C:
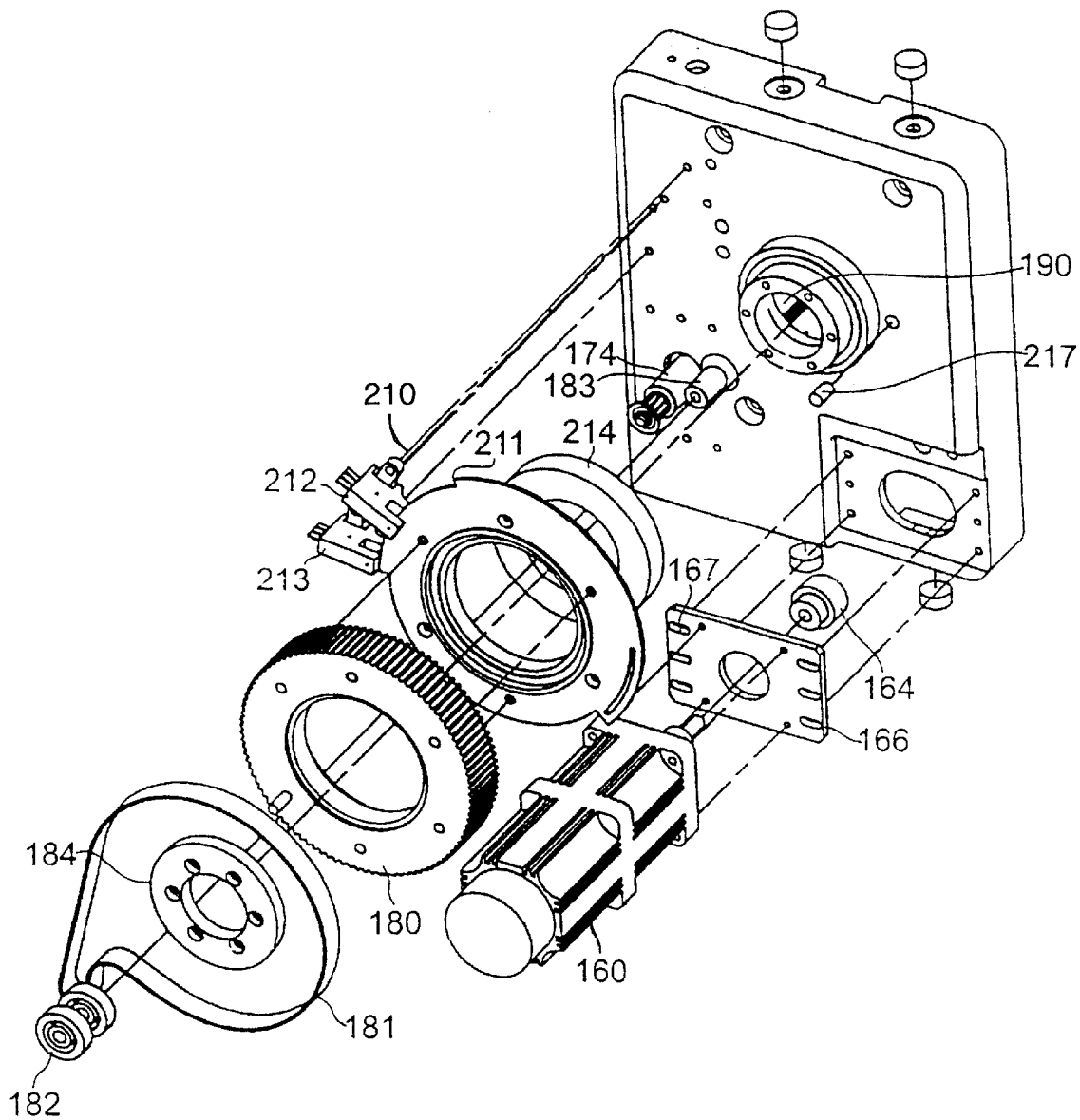
Figure 5D:
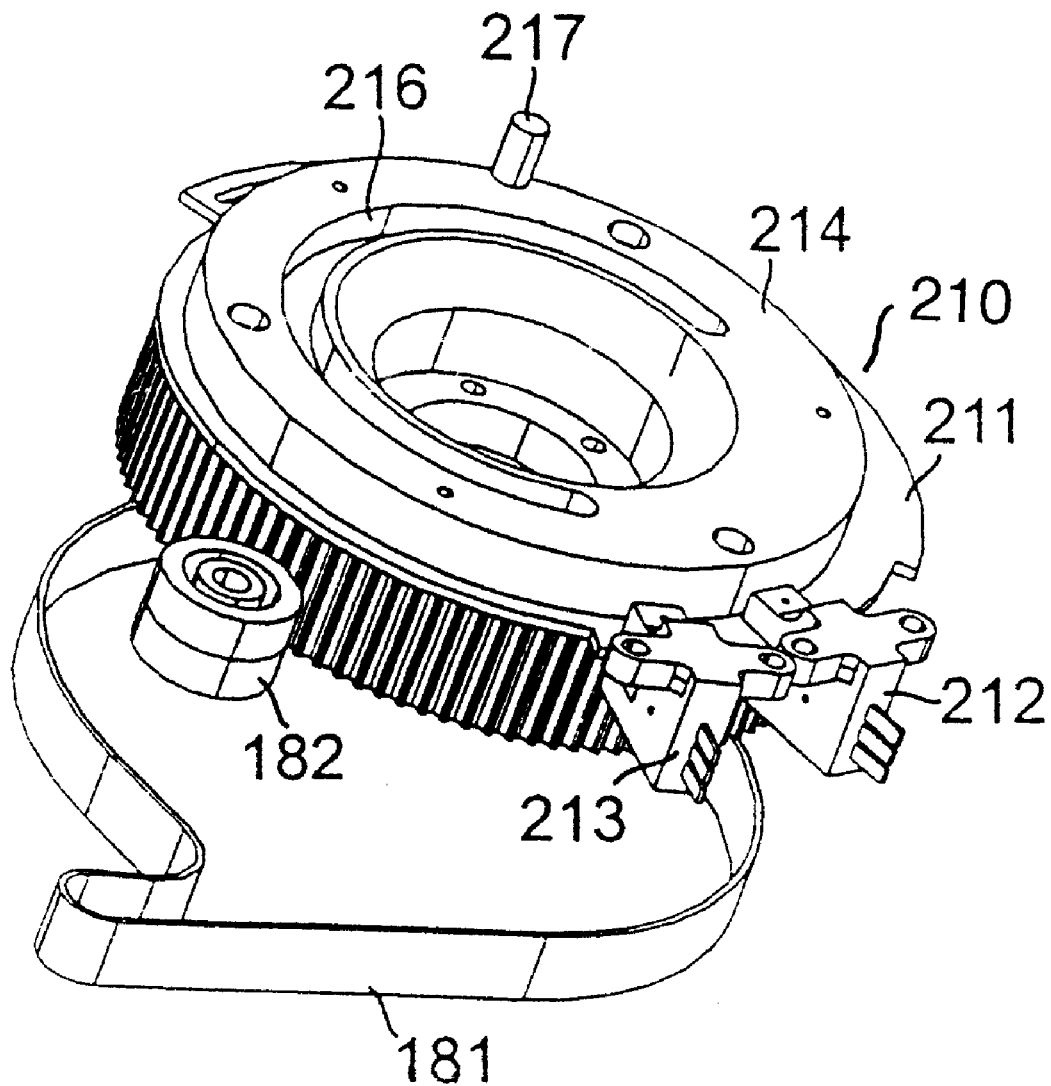
FIG. 5D is a top view of the theta homing plate mounted above the theta encoder ring.

The various components mounted between saddle platform 101 and thrust plate 184 are shown in an exploded view in FIG. 5C. An aperture 190 in saddle platform 101 extends downward from saddle platform 101 through the bottom of a circular projection 191 formed at the bottom of saddle platform 101. An absolute two-bit encoder is provided to create zones along theta over which it is safe to home as described below. The absolute encoder comprises an encoder ring 211 and two optical vane-type sensors 212, 213. Sensor 213 is mounted farther from the center of encoder ring 211 than sensor 212. The operation of encoder 210 will be described below. Homing in the theta direction is achieved by a homing plate 214 mounted to encoder ring 211, and planetary gear 180 and homing stop pin 217 extending from saddle platform 101 (FIG. 5D). Homing stop pin 217 on the bottom of saddle platform 101 is positioned within an arcuate slot 216 on homing plate 214. Kit motor housing 220 (FIGS. 5A and 5B) is mounted to the bottom of planetary gear 180, and the top of lead screw bracket 190 is mounted to the outside of housing 220 at point 222 on connector 221. (FIG. 5A)

The activation of theta-motor 170 causes the rotation of planetary gear 180 and the theta rotation of robotic arm 100. The theta range of movement is limited to less than 360 degrees to avoid hitting a possible back wall on instrument 10. In the illustrated embodiment, the theta range of movement is limited by homing stop pin 217 inserted in slot 216 which extends around only a portion of homing plate 214.

Figure 5E:
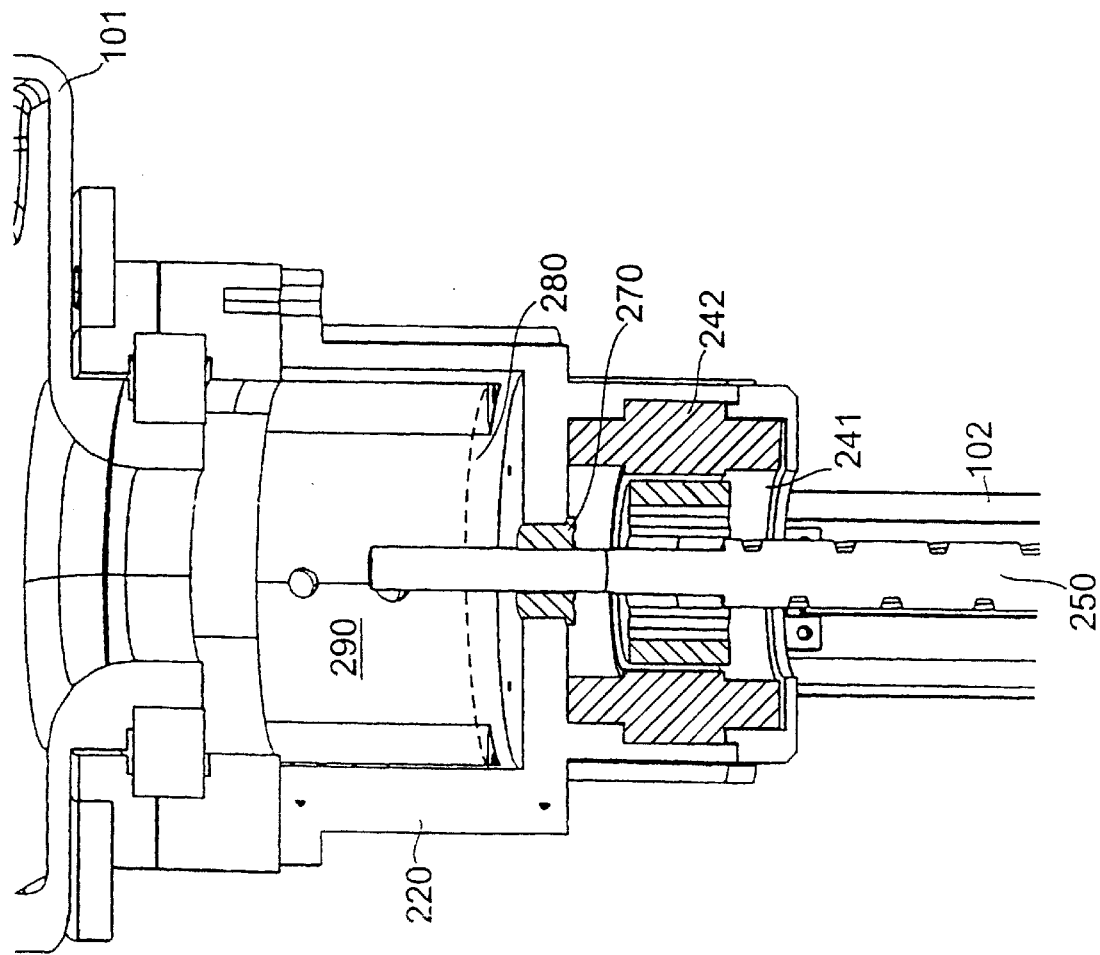
FIG. 5E is a cross-sectional view along line 5—5 of FIG. 2 of the kit motor housing surrounding the upper portion of the robotic arm including the z-motor.
Figure 5F:
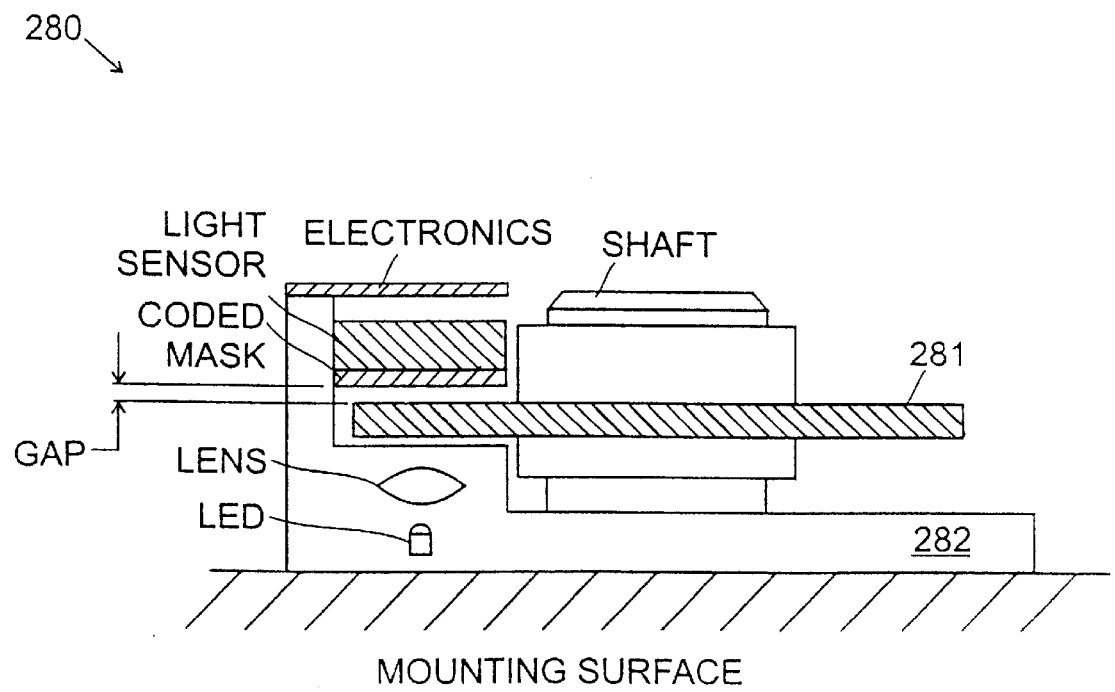
FIG. 5F is a side view of an incremental encoder that may be used to track the position of the gripper arm along the z-axis.

A "z-motor" 240 raises and lowers gripper arm 103 in the z-direction. Z-motor 240 is preferably a brushless closed-loop servo motor assembled below saddle platform 101 from a kit motor. The kit motor comprises a rotor 241 that is press fit onto a lead screw 250 and a stator 242 that is press fit to the inside of kit motor housing 220. FIG. 5E) One suitable kit motor for z-motor 240 is manufactured by MFM Model No. K032. An incremental encoder is also provided to track the position of robotic arm in the z directions.

Figure 2:
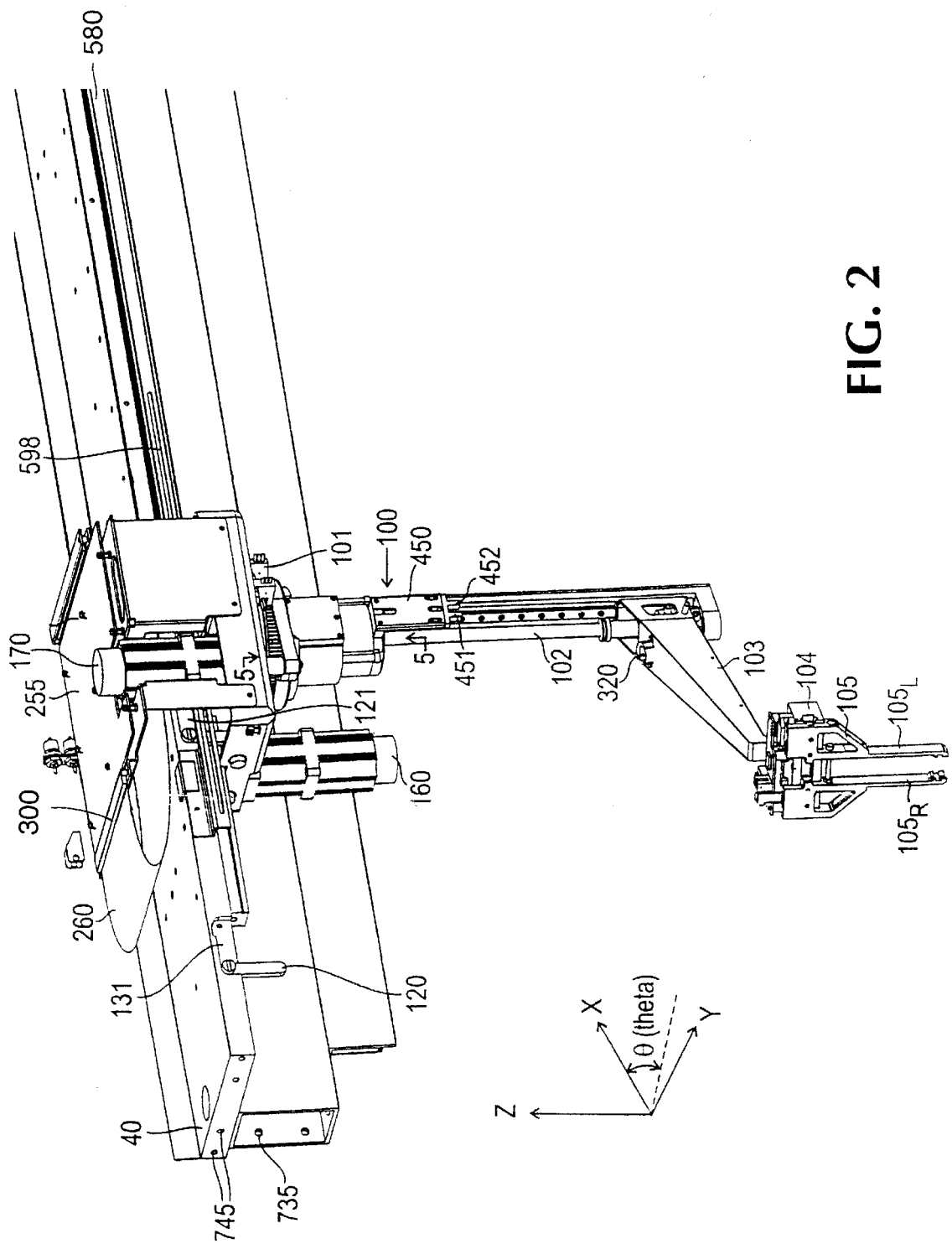
FIG. 2 is an isometric view of the robotic arm of FIG. 1 mounted to the beam with the gripper arm fully lowered.

Motors 160, 170 and 240 are conventionally powered and controlled by standard power distribution and servo control cards mounted in a tray (not shown) on instrument 10 and connected to a wiring harness 300 with a laminated, flexible cable 260 (FIG. 2). The servo circuitry permits the detection of obstructions to the motion of robotic arm 100 and position loss. If an error is detected, a recovery procedure to attempt homing of robotic arm 100 (in the particular dimension in which it was detected) that caused the error is initiated to resume normal operation. If the circuitry is unable to recover, robotic arm 100 stops moving and the user is alerted.

Cable 260 is preferably cambered for smoother, controlled movement of the cable as robotic arm 100 moves along rail 113. As shown in FIG. 2, wiring harness 300 is connected to cable 260 above an L-shaped plate 255 mounted to saddle platform 101 and overhanging beam 40.

Controlling the operation of instrument 10 are multiple controllers. Preferably, one controller, such as a controller from Galil of California, Model No. DMC1503 or a similar controller, is used for each robotic arm (i.e., both robotic arm 100 and robotic arm 200 referenced below) to store parameters and profiles for controlling the robotics. A separate master microcontroller for sample handler 20, such as a microcontroller based on the Intel 386EX processor, communicates with controllers for the other modules 31, 33 and 34 via a standard CAN bus and performs various mathematical calculations that may be required to operate the robotics.

Mounted above the z-motor 240 and within kit motor housing 220 is a bearing 270 through which lead screw 250 passes and mounted above bearing 270 is an optical encoder 280 with commutation tracks for measuring the rotation of z-motor 240 and thereby tracking the movement of gripper arm 103 along the z-axis. The top of lead screw 250 terminates within the center of optical encoder 280.

One suitable optical encoder 280 for z-motor 240 is the RCM15 Commutation 1.5" encoder manufactured by Renco of Goleta, Calif. Optical encoder 280 has commutation tracks in quadrature (i.e., the commutator has four zones demarcated by two rows of commutation tracks around the circumference of a glass disk which rotates within optical encoder.) Glass disk 281 is fit onto lead screw 250 and is driven by the rotation of lead screw 250. The body 282 of optical encoder 280 is mounted within kit motor housing 220.

A space 290 is left in housing above optical encoder 280 for wiring from wiring harness 300 which passes through an aperture 190 in the bottom of saddle platform 101 and into space 290. Wiring harness 300 passes out the bottom of kit motor housing 220 at 310 (FIGS. 4C and 5B) and enters the top of gripper arm 103 through an aperture 320. (FIG. 6A) Wiring harness 300 then passes within gripper arm 103 to gripper actuator 104. In this manner, wiring harness 300 does not interfere with the movement of robotic arm 100.

Gripper arm 103 extends the reach of fingers 105 to reach all areas of instrument 10 to and from which containers are to be moved by robotic arm 100. In the preferred embodiment, the reach does not extend to the front area of the instrument. Containers are fed into and out of the robot-accessible areas of sample handler 20 by the sample handler itself and containers are transported toward the front of the analytical modules, such as modules 33, 34 on a rack 37 on shuttle 38.

Gripper arm 103 may be sloped downward from its proximal to distal ends to reduce the required length of lead screw assembly 102 and thereby minimize interference posed by possible components or other obstructions situated under lead screw assembly 102.

FIG. 6B illustrates the coupling of lead screw assembly 102 to a fully-lowered gripper arm 103. A zero lash plastic slip nut 330 that is threaded on the inside is placed onto lead screw 250. A brass cylindrical insert 340 that is threaded on both its interior and exterior is threaded on its interior onto slip nut 330 and glued to slip nut 330. Insert 340 is inserted through a hole 350 in the bottom of gripper arm 103 and a split collar 360 is tightened to the bottom of insert 340 to lock gripper arm 103 to insert 340.

The bottom of lead screw 250 sits in a bearing 370. Bearing 370 is held in place with an adjustment nut 380 tightened to the bottom of lead screw bracket 190. A circular wave spring 390 is inserted between adjustment nut 380 and lead screw bracket 190 to accommodate thermal expansion in lead screw 250. A void 400 is left between the bottom of lead screw 250 and adjustment nut 380 to permit the rotation of lead screw 250.

Threading on lead screw 250 preferably moves gripper arm 103 12½ mm per revolution of lead screw 250 to provide a smooth motion and lessen the effects of the inertia of a load on the motion of gripper arm 103. The threading also provides precise control over the vertical movement of gripper arm 103.

Figure 7:
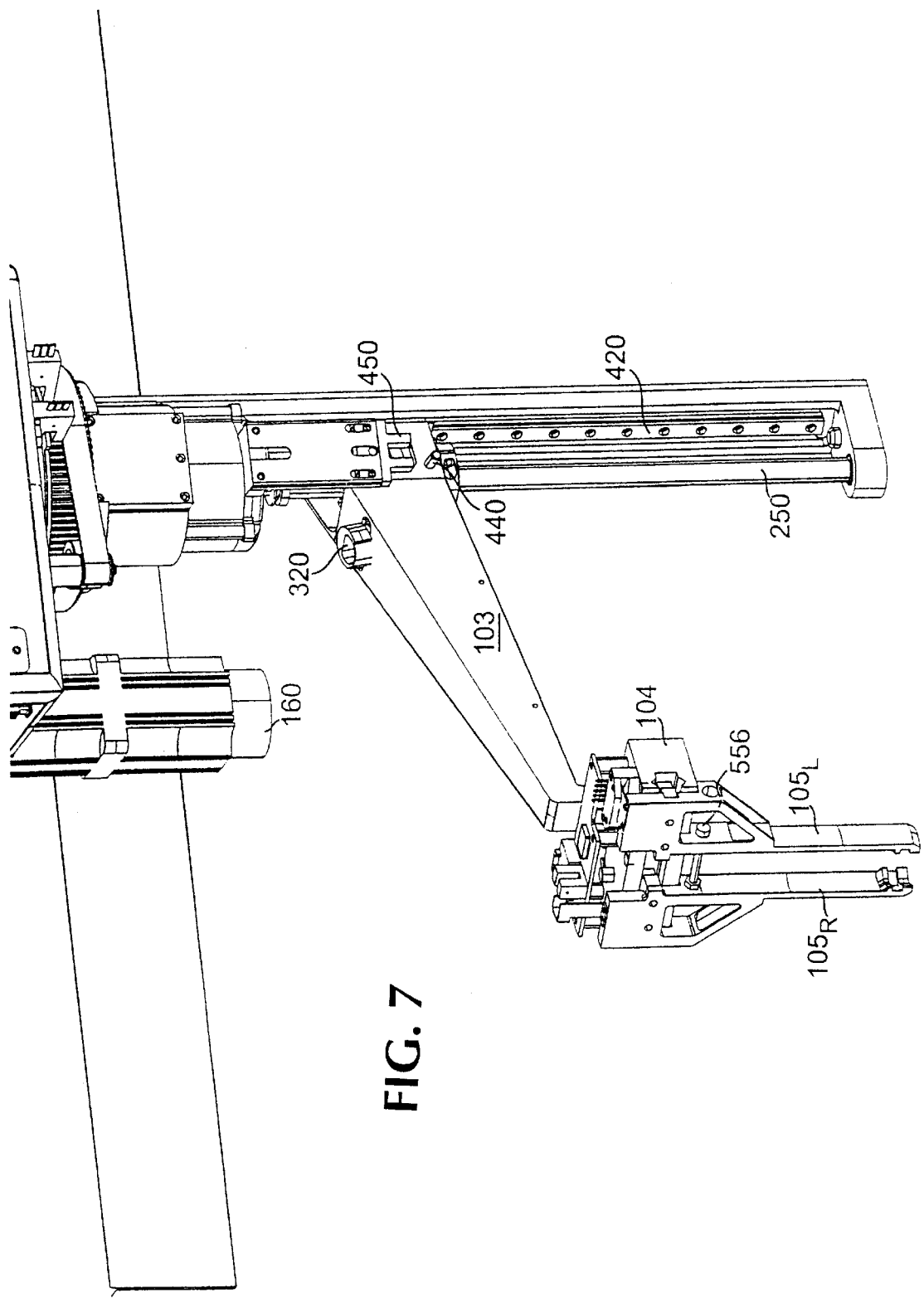
FIG. 7 is a perspective view of robotic arm with the gripper arm raised along the lead screw assembly.

To raise gripper arm 103, z-motor 240 is activated in a first direction causing lead screw 250 to rotate. Two pillow blocks 410, 411 at one end of gripper arm 103 slide along a rail 420 (FIG. 7) mounted to lead screw bracket 190. If gripper arm 103 is fully raised, the top of upper pillow block 410 hits a hard stop 430 along rail 420 and a pin 440 that functions as a z-axis homing flag on the side of gripper arm 103 engages within a plug-shaped, through-beam infrared sensor 450. This interrupts an infrared light beam, which is transmitted out of a transmitter on one side 451 of sensor 450 and otherwise received on the other side 452 of sensor 450 (FIG. 3B).

To lower gripper arm 103, z-motor 240 is activated in the opposite direction. A hard stop 460 is mounted to the bottom of lead screw bracket 190 (FIG. 6B). An insert 470 is press fit into the bottom of gripper arm 103 adjacent rail 113 to reference (i.e., contact) hard stop 460 if gripper arm 103 is fully lowered along lead screw bracket 190.

Figure 8A:
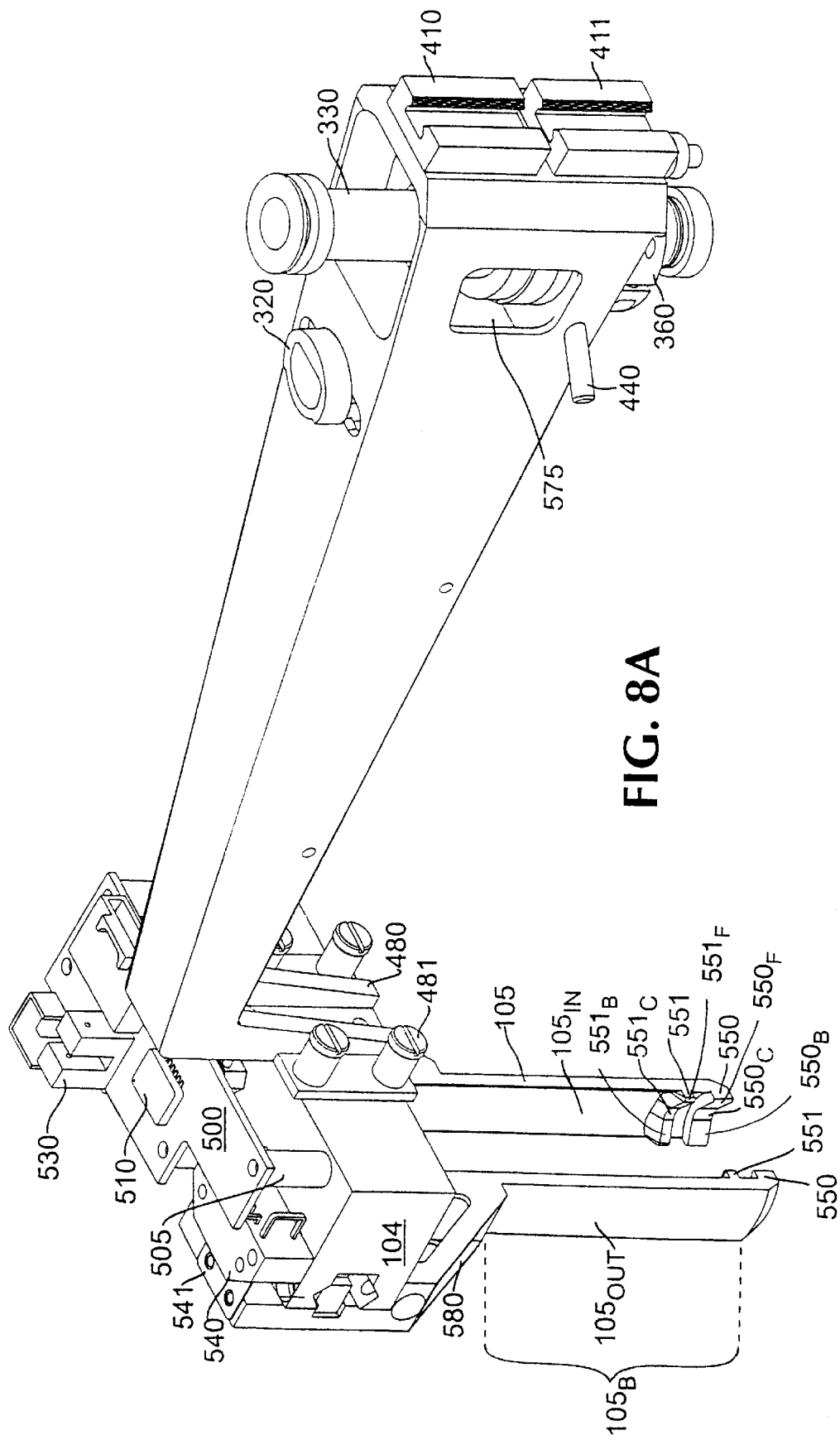
FIG. 8A is an isometric view of a gripper arm from the left side of the gripper arm.
Figure 8B:
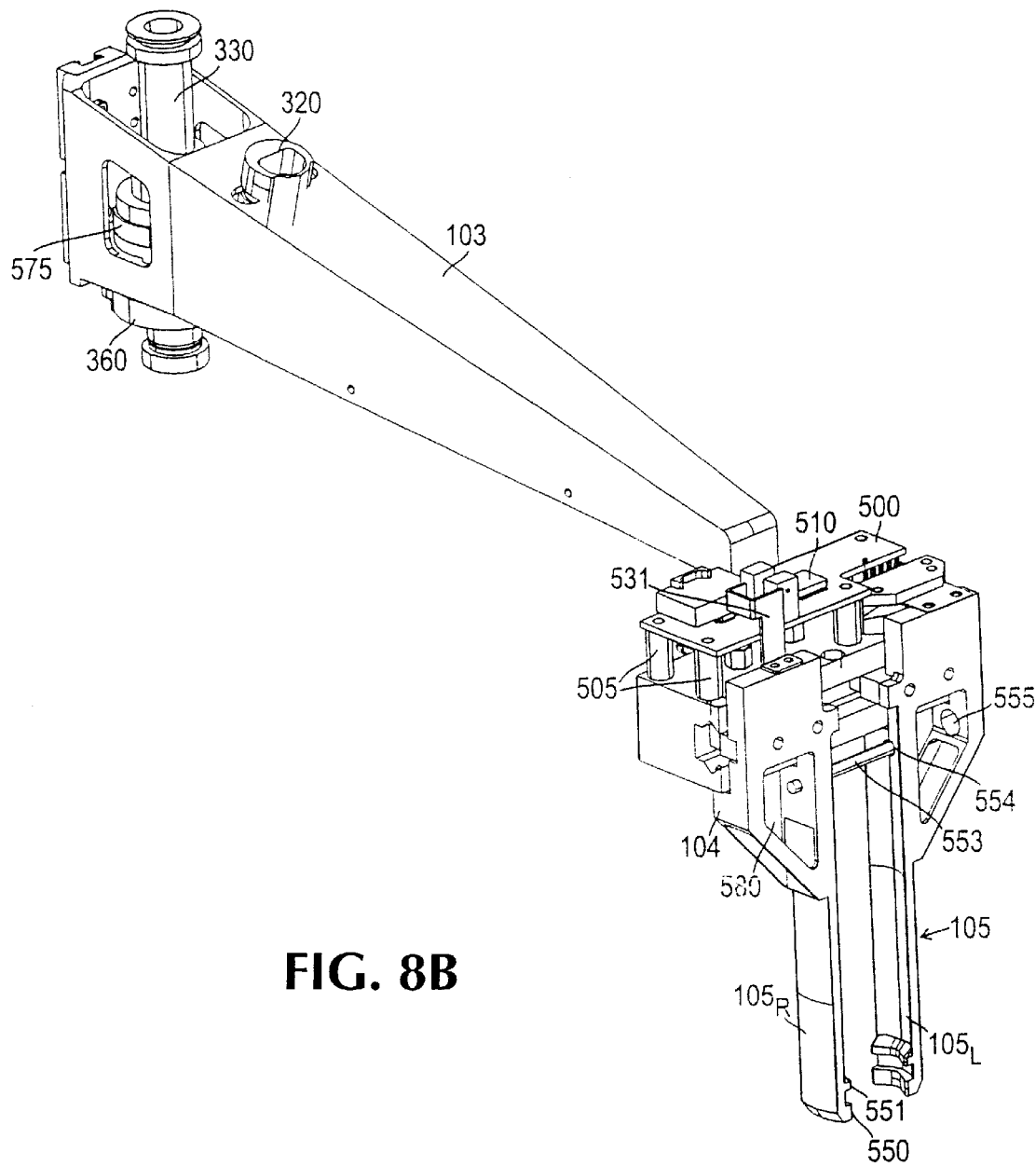
FIG. 8B is an isometric view of the gripper arm from the right side of the gripper arm.

A vertical mount area 480 is provided on the outer end of gripper arm 103 for mounting gripper actuator ("grippers") 104, which is a conventional parallel grippers. (FIGS. 8A and 8B) The back of grippers 104 mount to the front of vertical mount 480. Grippers 104 are designed to be easily removable for replacement or service by the removal of four thumb screws 481. Grippers 104 are a horizontal grippers, as opposed to a vertical grippers, to provide space on top of grippers 104 for mounting a printed circuit board 500 with various electronics components. One suitable grippers is model RPL-3 manufactured by Robohand Inc. of Monroe, Conn. Fingers 105 are mounted to the front of grippers 104.

Printed circuit board 500 is mounted to posts 505 that are mounted to the top of grippers 104 and various electronic components are mounted to the top of printed circuit board 500, including an inertia switch 510, an optical vane-type sensor 530, such as an infrared through-beam sensor, and an incremental encoder 540. Inertia switch 510 immediately detects a collision between fingers 105 or grippers 104 and some other object and to immediately stop the movement of grippers 104. Sensor 530 detects when grippers 104 are fully closed when infrared beam on sensor 530 is interrupted by a U-shaped flag 531 that is mounted to the top of one of fingers 105, the right finger in the illustrated embodiment. Printed circuit board 500 processes signals received from inertia switch 510, sensor 530 and encoder 540 and communicates with the controller for robotic arm 100.

Encoder 540 tracks the opening and closing of grippers 104 and thereby determines the width of the container which is gripped by grippers 104 by determining the size to which gripper 104 remains after gripping a container. Encoder 540, which may comprise an encoder manufactured by Hewlett-Packard as Model HEDS 9100, preferably has two infrared beams spaced apart from one another that both counts the number of tracks on a plate 541 (FIG. 8D), mounted to the top of fingers 105, which passes sideways through encoder 104 as grippers 104 open and close. Plate 541 is transparent except for a pattern of parallel black lines spaced from each other by a width equal to the width of a line equidistantly. Infrared beams on encoder 104 are spaced apart from each other out of phase by 90° to generate identical signals 90° out of phase and to increase the precision of the measurements to half the width of a line. Whether grippers 104 are opening or closing may be determined from the shape of the signal generated.

In an alternative embodiment, shown in FIG. 9 without a printed circuit board or other electronics mounted to gripper 104', vertical grippers 104' are mounted to a horizontally-positioned mount area on a slightly different gripper arm 103'. The top of a grippers 104' mounts to the mount area on gripper arm 103' and fingers 105' mount to the bottom of grippers 104'. However, this embodiment may not leave enough space to mount the electronics thereon.

Grippers 104 are pneumatically operated with air ports (not shown) to inject air into a double action air cylinder in grippers. Pressure applied on one side of the cylinder opens grippers 104 along with fingers 105 and pressure applied on the other side of the cylinder closes grippers 104 and fingers 105. Grippers 104 maintain a closed position when not in the process of picking up or releasing a container so as not to drop the container if air pressure is lost while holding the container.

Figure 11A:
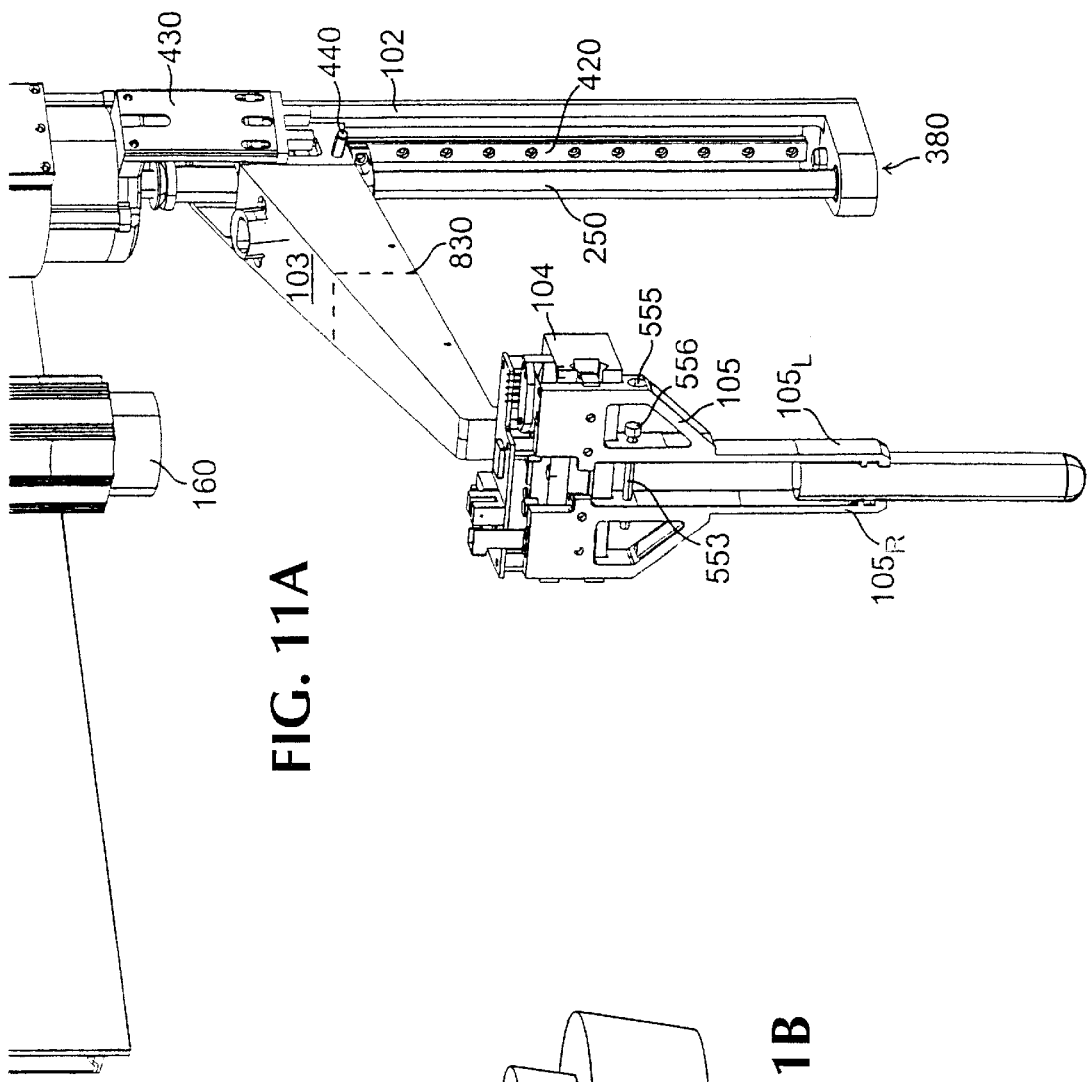
FIG. 11A is a perspective view of the robotic arm gripping a test tube.

Valves and air tubes (not shown) are located as close as possible to robotic arm 100 to be able to respond to the activation of grippers 104 as quickly as possible. When otherwise unconstrained, grippers 104 may open more than is desirable and than the manufacturer's specifications for the grippers such that the outer side of fingers 105 might hit an adjacent container or obstruction. Therefore, referring to FIGS. 8B and 11A, a means for limiting the separation of fingers 105 independently of grippers 104 is incorporated into fingers 105. The limiting means consists of a rod 553, mounted to the inner face of one of the fingers 105, such as left finger $105_L$, that passes through a corresponding hole 554 on the inner face of right finger $105_R$. Rod 553 has a stop 556 at the end that is larger than hole 554 and limits the opening of fingers 105. When fingers 105 are closed, stop 556 extends into a hole 555 on the outer face of finger $105_R$ that provides clearance for stop 556.

The gripping force of grippers 104 should preferably be limited, such as to a range of 25–30 psi, to minimize the deflection of fingers 105 and limited so that it does not exceed 50% of the force necessary to crush the weakest test tube that will be used in instrument 10.

Figure 12:
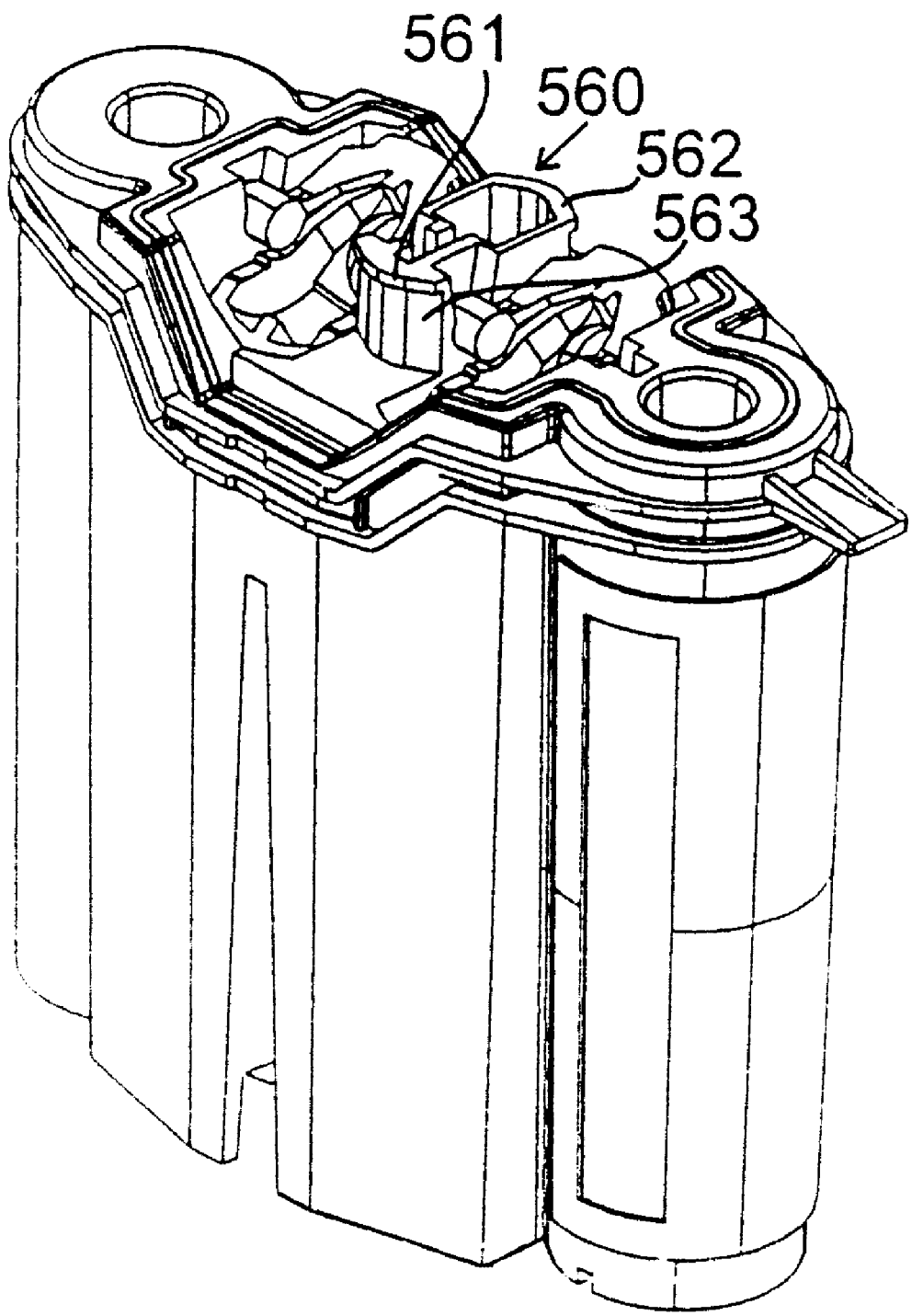
FIG. 12 is an isometric view of a reagent package having a gripping block from which fingers on robotic arm may grip the package.
Figure 13:
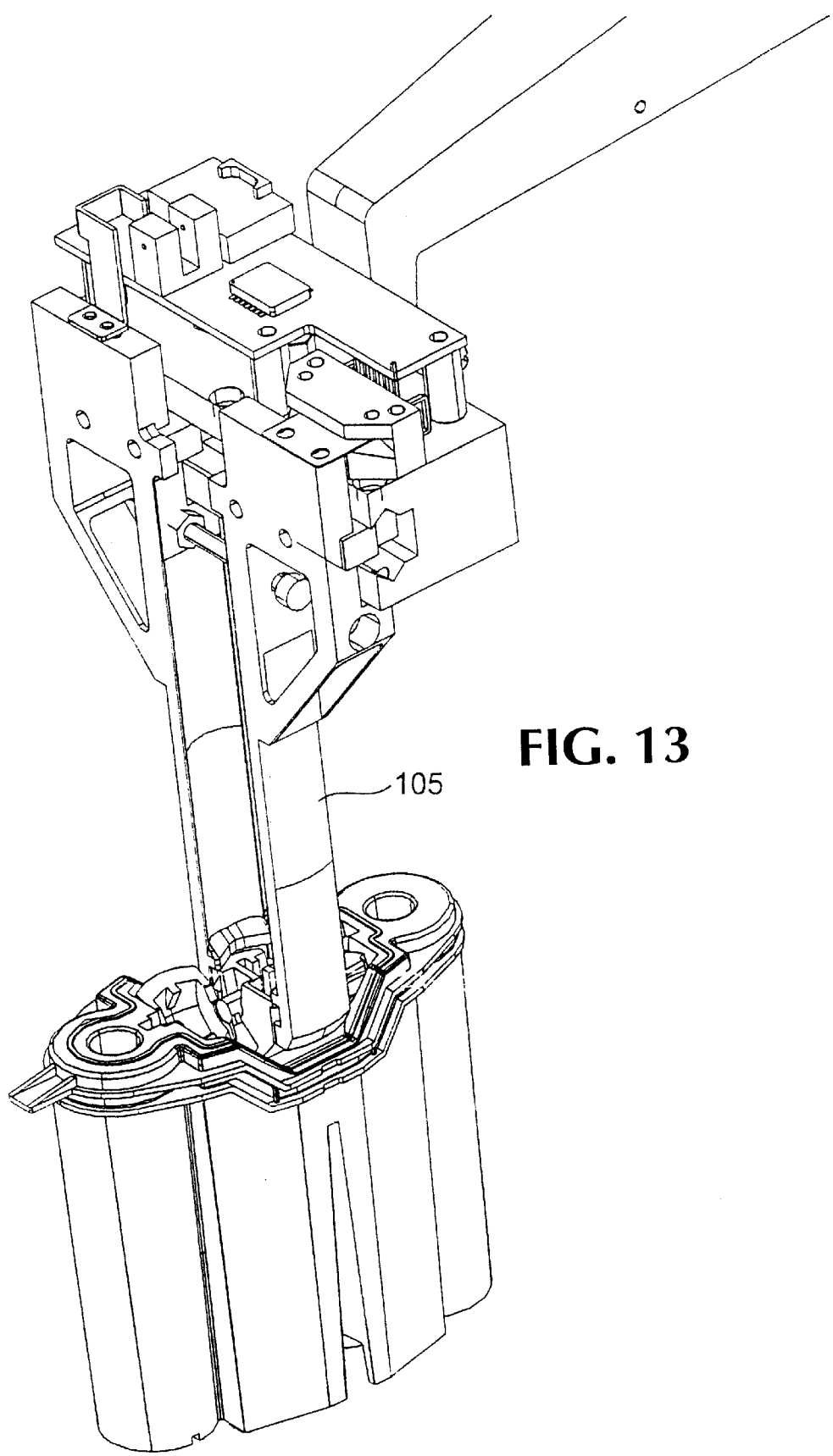
FIG. 13 is an isometric view of fingers gripping the reagent package of FIG. 12.

Robotic arm 100 is designed to transport the various containers referenced above. Fingers 105 must therefore be versatile and strong enough to resist bending by the heaviest load placed on robotic arm 100. Fingers also must be compact enough to avoid hitting obstructions while moving containers into and out of areas with tight clearances. For example, reagent packages as shown in FIGS. 12 and 13 (such as the package described in application Ser. No. 08/985,759) may be inserted through an opening 33a in a cover 33b on top of clinical analysis module 33 and into a carousel (not shown) under cover 33b. Opening 33a may be only several millimeters wider than the reagent package and fingers 105 must clear opening and have some clearance to insert the reagent package into the carousel. As another example, fingers 105 must be able to insert a diluent package, which contains diluent (application Ser. No. 29/088,045) and is less than half the size of the reagent package through opening 31a in a cover 31b on module 31, which is smaller than opening 33a, and into a particular position on another carousel (not shown) on module 31. Fingers 105 must also be long enough so that grippers 104 never descends below any cover on an analytical module where environmental conditions could damage it.

Figure 10:
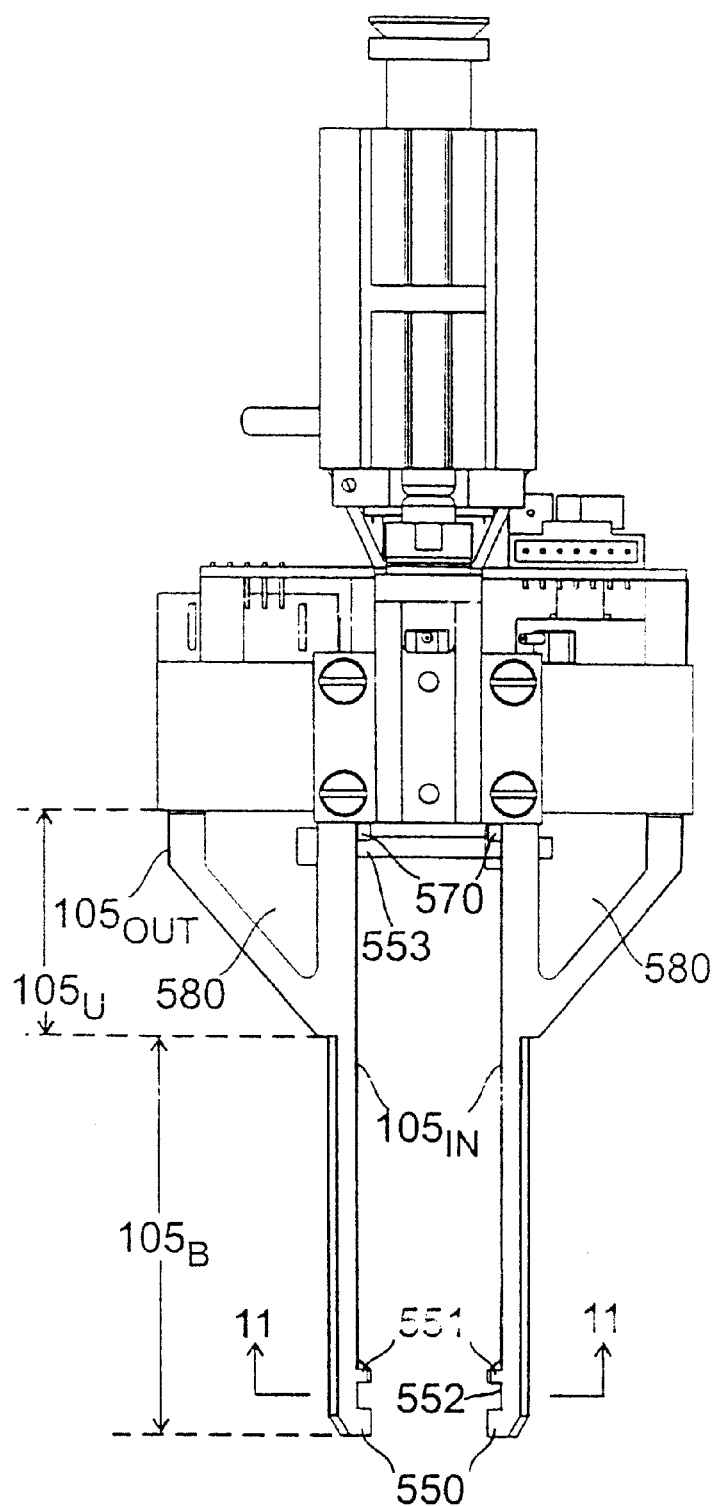
FIG. 10 is a rear view of a gripper arm shown in FIG. 8.

Each of the two fingers 105 are almost identical. Fingers 105 are shaped as shown in FIG. 10 with a pentagonal upper portion $105_U$ and a narrower lower portion $105_B$ extending vertically downward. The wider top surface of fingers $105_U$ provides more stability to fingers while the much narrower lower section $105_B$ allow fingers 105 to move within tight spaces. When grippers 104 are opened, the top of upper portion $105_U$ opens outward over the bottom surface of grippers 104 to a width such that the outermost edge $105_{out}$ of each finger 105 when grippers 104 are fully open does not extend beyond the sides of grippers 104.

Figure 8C:
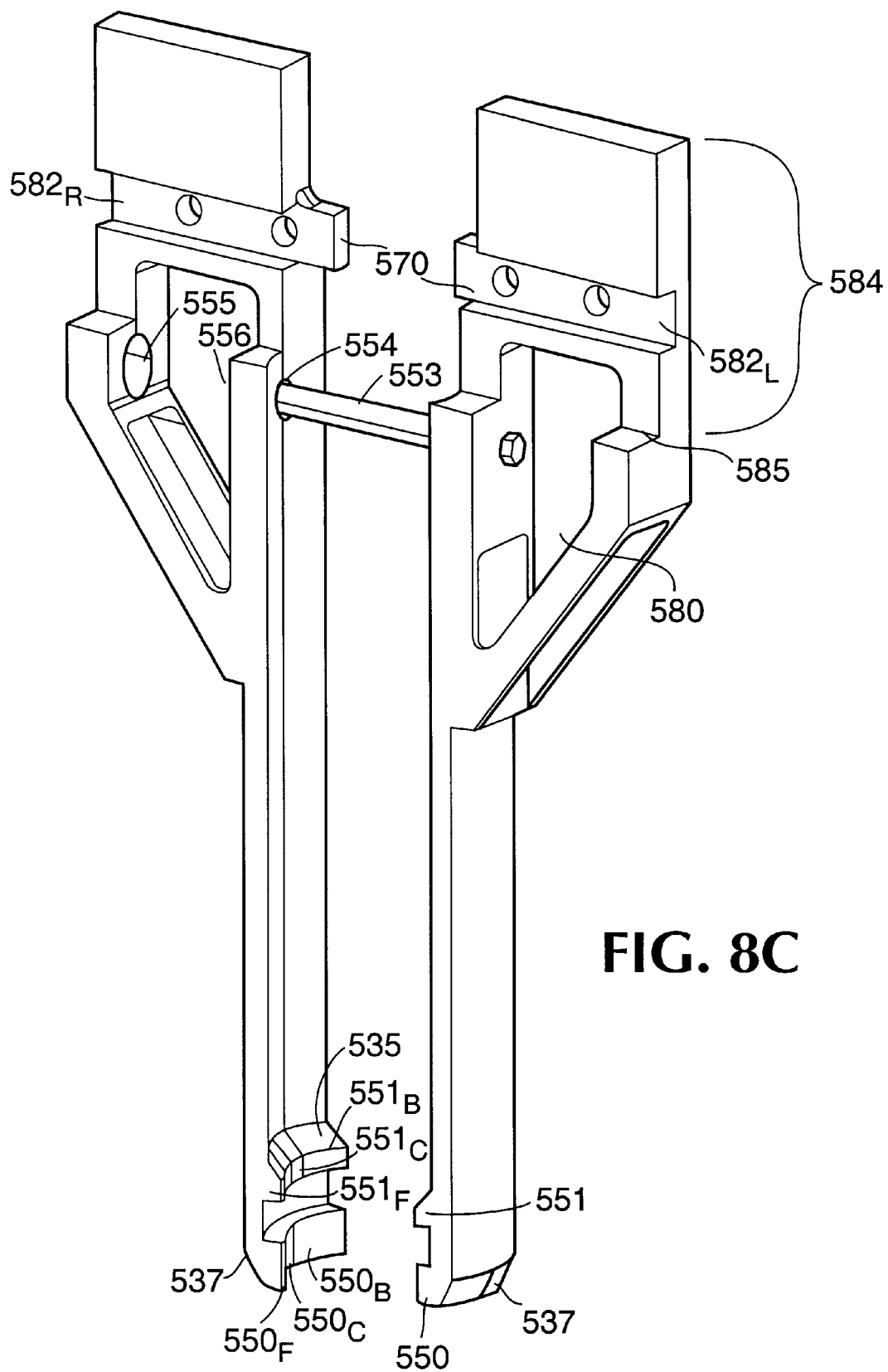
FIG. 8C is a rear view of the gripper fingers.
Figure 8D:
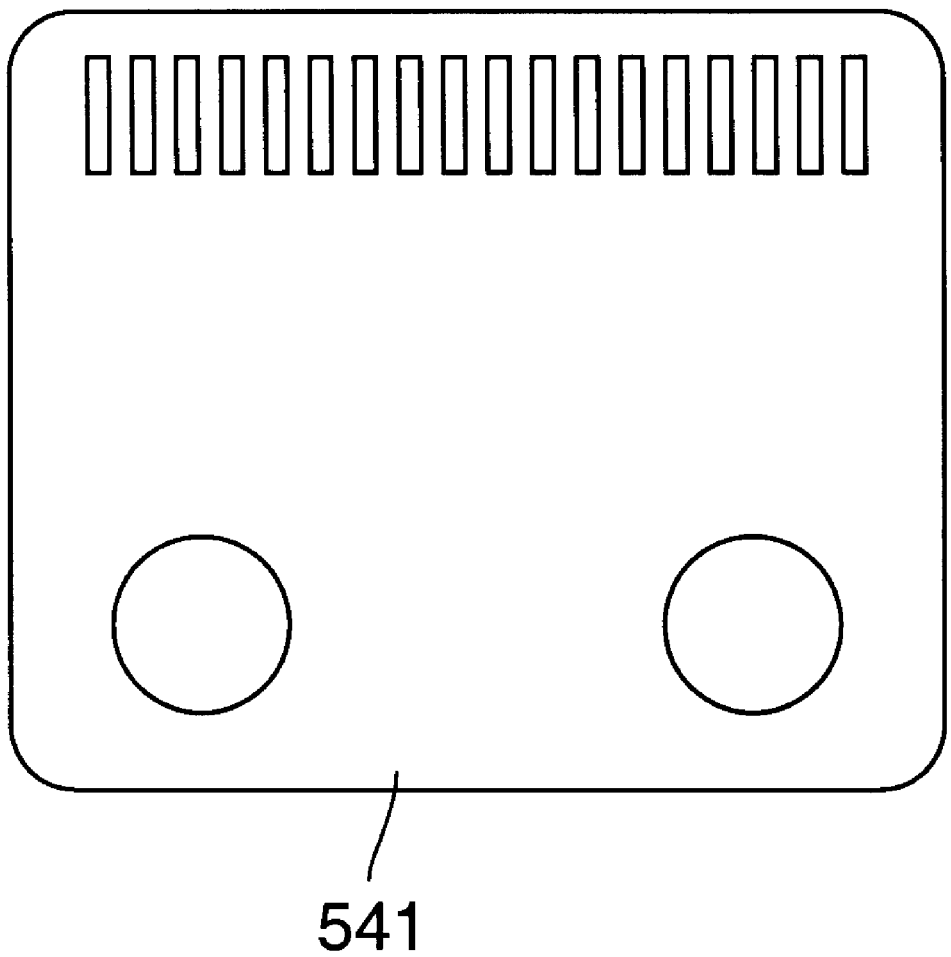
FIG. 8D is a top view of the encoder plate mounted to the fingers.

Referring to FIG. 8C, fingers 105 mount to grippers 104 at grooves $582_R$ and $582_L$. To keep fingers 105 as narrow as possible to fit into an area with little room to maneuver, the thickness of fingers 105 is reduced in a top portion 584 and at point 585 the fingers 104 widen so that when fingers 105 are mounted to grippers 104 the lower portion of fingers 105 below point 585 wraps below grippers 104.

To grip the various containers used with instrument 10, two projections 550, 551 extend inward from fingers 105 with a groove or channel 552 left between the projections. Upper and lower projections 550, 551 are flat on top and bottom and are contoured identically on their innermost sides to have central sections $550_C$, $551_C$ which may be curved and front and back sections $550_F$, $551_F$ and $550_B$, $551_B$, respectively, which have a straight edge and are angled from one another at approximately 120° (the zero reference point of the angle being at the center of center sections $550_C$, $551_C$). The central sections $550_C$, $551_C$ are preferably curved at a radius of 3 mm to better grip front and rear walls on the gripping block 560 on reagent and diluent packages described below. The angle between front sections $550_F$, $551_F$ and back sections $550_B$, $551_B$ is selected so that fingers 105 do not break a test tube when they close around a test tube, which might otherwise occur if the angle between front and back sections $550_F$ and $550_B$ were less than 120°. Upper and lower projections 550, 551 extend an additional approximately 4 mm inwards beyond the 1 mm thickness of the lower portion $105_L$ of fingers 105. The inner-facing side $105_{IN}$ of each of fingers 105 is curved. (FIG. 8) The contour of side $105_{IN}$ and its setback from upper and lower projections 550, 551 allows the secure gripping of a test tube while leaving clearance for a cap or other closure on a test tube so that the cap or closure does not contact side $105_{IN}$, which could cause the cap or closure to stick to fingers 105 and interfere with the release of the test tube in its destination location. The 4 mm difference in diameter between upper and lower projections 550, 551 and side $105_{IN}$ is thought to be sufficient for caps on most currently-manufactured test tubes that may be used with instrument 10. However, if caps on various test tubes do contact side $105_{IN}$, the difference in diameter between upper and lower projections 550, 551 and side $105_{IN}$ may be enlarged.

A beveled edge 535 between upper projection 551 and side $105_{IN}$ accommodates caps or closures on short test tubes, such as 75 mm test tubes, which the robotic arm 100 picks up with the lower edge of screw-on caps positioned directly above upper projection 551 when a test tube is gripped so the caps preferably do not touch upper projection 551. Another beveled edge 537 at the bottom outer edge of fingers 105 prevents the fingers 105 from breaking a first test tube if fingers 105 knock into that first test tube while picking up a second test tube adjacent the first test tube.

The height and width of lower projection 550 is also selected to be able to grip a predilution cup 564 described in the Cup Handling System application and further described below, and the height and width of upper projection 551 is selected to be equal to the width of lower projection 550. In a preferred embodiment, for reasons explained below, the height of upper and lower projection 551, 550 are respectively, approximately 2 mm and 4 mm. Groove 552, separating upper and lower projections 550, 551, is approximately 4 mm high.

When grippers 104 are opened, rod 553 limits the opening of fingers 105 so that the exterior sides of fingers 105 separate from each other approximately 30 mm, as shown in FIG. 10. Because of the approximately 5 mm thickness of lower and upper projection 550, 551, the maximum diameter of test tubes, incubator covers or other round containers that may be gripped by fingers 105 is approximately 20 mm. Due to slight variation in the length of projections 550, 551, the maximum diameter may be as large as 20.5 mm.

For non-round containers or round containers larger than 20 mm in diameter, a gripping block or other gripping means, preferably including a flange, must be provided on the containers for robotic arm 100 to lift them. One particular gripping block 560 may be provided on the top of a reagent package, which contains reagents used by instrument 10. This particular reagent package is described in more detail in application Ser. No. 08/985,759 (which refers to gripping block 560 as "pivot block 110"). Gripping block 560 has a front wall 563 and a back wall (not shown but shaped like front wall 563) which is curved to fit within the contour of fingers 105 and two curved flanges, front flange 561 and rear flange 562, which may follow the same curvature as the front and back walls. Where the maximum diameter between opposing upper and lower projections 550, 551 on left and right fingers $105_L$ and $105_R$ is approximately 20 mm, front and rear flanges 561, 562 must be separated from one another by a diameter of less than 20 mm in order to fit between fingers 105. The recesses and contours of the side walls of gripping means 560 as well as other details of the illustrated reagent package are not significant for the purposes of the present application. However, it is important that no elements adjacent the gripping means 560 interfere with movement of fingers 105 around flanges 561, 562. A similar gripping means may be used on other containers, such as the diluent packages.

Groove 552 serves to properly align an otherwise misaligned container at the time the container is retrieved. If a reagent package or other container with gripping block 560 or a similar means for gripping the container is not seated at its pick up location completely vertically when robotic arm 100 arrives to pick it up, projections 550, 551 and groove 552 help align the reagent package or other container as fingers 105 close around gripping block 560 by catching flanges 561, 562 of gripping block 560 in groove 552. The top of the flange that is raised too high hits the bottom of projection 551 and is pushed downward while the bottom of the other flange that is too low is pushed upward by the top of lower projection 550. Groove 552 between projections 550, 551 is sized to grasp the top flanges 561, 562 on opposite sides of gripping block 560, while providing some additional space allowance for realignment of the flanges and to prevent flanges 561, 562 from getting stuck in groove. Where flanges 561, 562 are approximately 1 mm thick, the 4 mm height of the groove provides the additional space allowance required for realignment. Sufficient clearance, at least approximately 7 mm, is left on gripping block 560 below flanges 561, 562 for the 4 mm height of lower projection 550 to grip gripping block 560 while also leaving space for realignment.

Stops 570 at the top front of fingers 105 face inward with fingers 105 installed on grippers 104. The stops contact each other when grippers 104 are closed to counteract the forces propagated through fingers 105 by the closing of grippers 104 and the resulting contact of upper and lower projections 550, 551 at the bottom of fingers 105, which otherwise cause fingers 105 to bend. Stops 570 extend inward approximately 4 mm which is the width of lower projection 550.

Figure 11B:
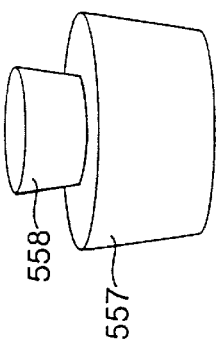
FIG. 11B is a perspective view of an incubator cover that may be gripped by the robotic arm.
Figure 11C:
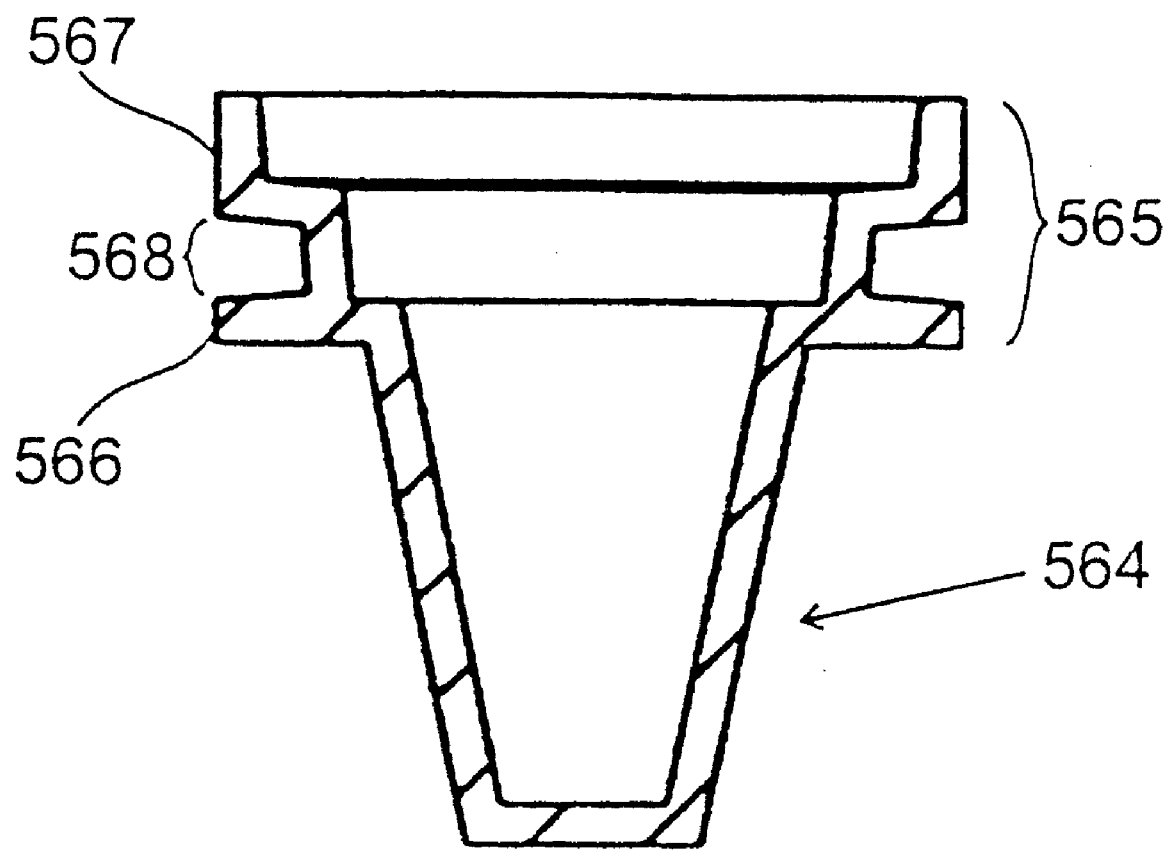
FIG. 11C is a perspective view of a predilution cup, which may be gripped by the robotic arm.

Other containers that may be gripped by fingers 105 include an incubator cover 557 used by instrument 10 (FIG. 11B) and the dilution cup 564 (FIG. 11C). Incubator cover 557 has a cylindrical gripping section 558 by which it is gripped. Cup 564 has a cylindrical upper portion 565 that includes a bottom flange 566, a top flange 567 and a groove 568 between flanges 566 and 567. Lower projection 550 is inserted within groove 568 and top flange 567 of cup 564 fits within groove 562 of fingers 105. The height of top flange 567 is sized to leave clearance for the upper surface of top flange 567 to self-align cup 564 during pickup.

Gripper arm 103 and fingers 105 are designed to be as lightweight as possible by construction with relatively light-weight materials and the use of various features that lighten gripper arm 103 and fingers 105. Therefore, gripper arm 103 preferably has apertures 575 on the sides of gripper arm 103 near lead screw 250. For the same reason, an opening 580 is preferably left within each of fingers 105 to lighten the weight of fingers 105.

As robotic arm 100 is designed to carry, among other things, open test tubes, movements of robotic arm 100 should prevent the jerking of test tubes or other movements which may cause the spilling of samples from open test tubes. Of further concern, movements of robotic arm 100 should not disturb samples, which may be incubated in one of modules in instrument 10. Therefore, the acceleration of robotic arm 100 in the x-direction along rail 113 when carrying a test tube should preferably not exceed 0.3 g to avoid spillage when carrying an open container such as a test tube. The acceleration may be increased to as much as 0.5 g if spillage is not found. When robotic arm 100 transports closed containers, including reagent packs, it may accelerate faster. This acceleration and deceleration should follow an S-curve-shaped acceleration profile to prevent jerk in robotic arm 100 from propagating to modules 20, 30–34 in instrument 10. When robotic arm 100 is not carrying a test tube it may accelerate faster, possibly as high as 1.5 g. Vertical up and down movements or gripper arm 103 along rail 420 may accelerate up to 1 g. Slew speeds and acceleration profiles for motors 160, 170 and 240 must also keep audible noise to a minimum.

Because robotic arm 100 transports containers between specific positions on instrument 10, it must track precisely where it is located. Moreover, in a typical analytical instrument with which robotic arm 100 may be used, there are likely to be areas, such as where other components of instrument 10 or beams or walls of the instrument are located, where certain movements of robotic arm 100 may be limited. Therefore, homing mechanisms are provided for each of the x-motor 160, theta-motor 170 and z-motor 240 to properly position robotic arm 100 to a known location after it is powered up or if robotic arm 100 collides with another object before resuming operation.

Robotic arm 100 may always be homed along the z-axis without any concern of hitting an obstruction because z-axis homing requires only that gripper arm 103 be fully raised. However, due to the layout of the components on various modules in instrument 10, robotic arm 100 cannot be homed in the x and theta directions in every location along instrument 10 as robotic arm 100 may hit an obstruction if it were homed in certain areas. In particular, homing in the theta direction requires a large rotation of gripper arm 103 in the theta direction, which on homing plate 214 is approximately 270°. The layout of instrument 10 in the configuration shown in FIG. 1, creates some spaces where robotic arm 100 cannot be fully rotated over 270° in the theta direction, and other spaces where robotic arm 100 may be homed in the theta direction.

The first step in the homing process is to home gripper arm 103 along the z-axis. Typically, this simply entails raising gripper arm 103 from whatever position it is previously in along the z-axis and gripper arm 103 is detected to be in a home position when pin 440 on gripper arm 103 passes through an infrared beam in through-beam sensor 450. Sensor 450, however, uses "fine edge" detection, meaning that it only detects the front edge of an object moving upward through the bottom edge of the infrared beam so if gripper arm 103 is already fully raised at the start of the homing process it is not detected. Thus, when gripper arm 103 is fully raised before homing begins, gripper arm 103 is lowered slightly beneath sensor 450 and is then returned to its original fully-raised position. (FIG. 6).

The homing mechanism next determines if it can be homed in the x and theta directions. The primary concern in horning in the x-direction is that robotic arm 100 be able to travel the full length of rail 113 without gripper arm 103 hitting an obstruction, including a side wall of instrument 10. The primary concern in homing in the theta direction is that robotic arm 100 not hit an obstruction as it pivots about lead screw 250.

Figure 15:
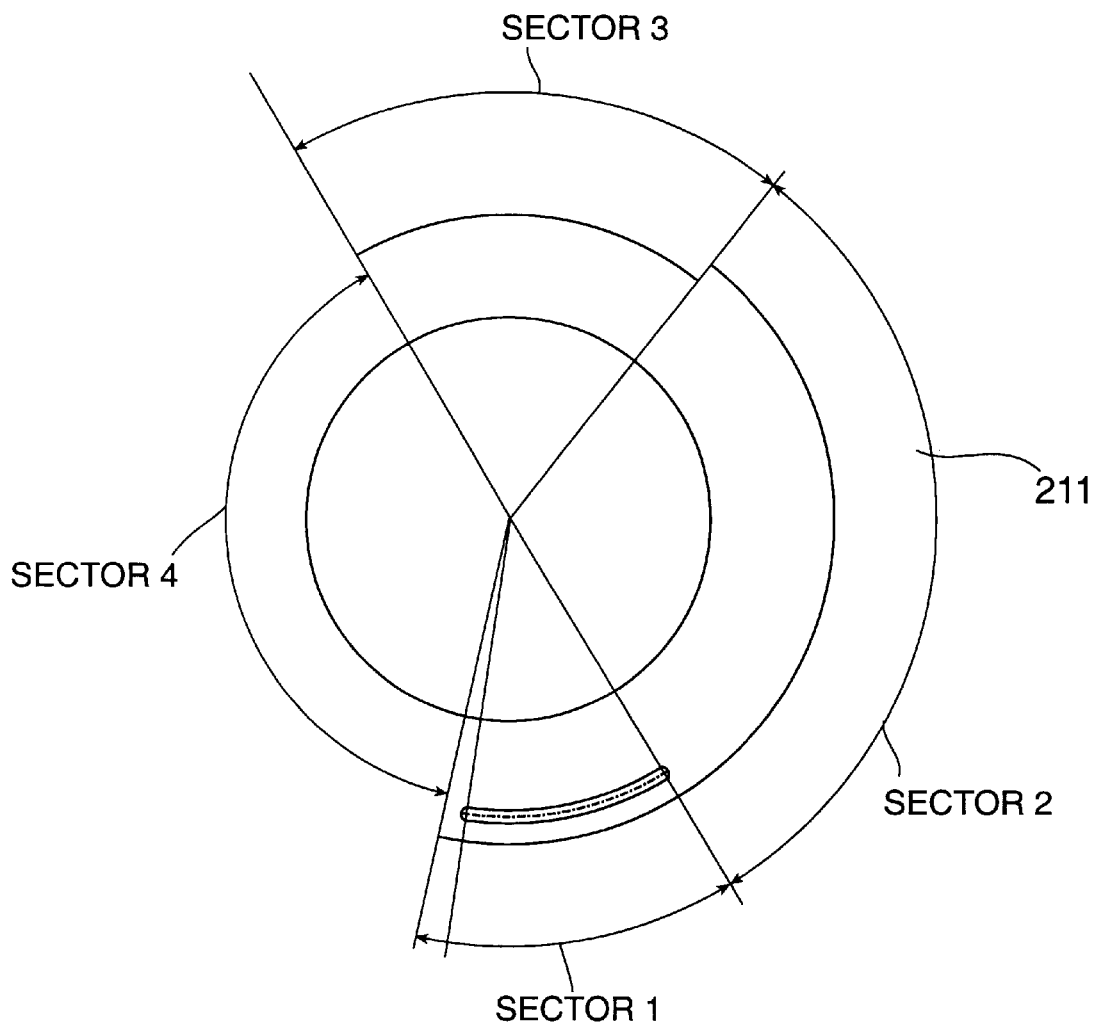
FIG. 15 is a top view of theta homing plate.

An absolute two-bit encoder comprising encoder ring 211 and sensors 212, 213 adjacent encoder ring 211 provide the information required to determine if it is safe for robotic arm 100 to home in the x direction. Encoder ring 211 defines four sectors 14 (FIG. 15). The size of the sectors may vary but are selected so that movement is permitted in those sectors in which gripper 103 will not hit an obstruction when robotic arm 100 is moved in the x-direction along rail 113 These sectors will generally be confined to areas under beam 40. Thus, in the illustrated example, sector 1 covers an arc over the left side of the rear of instrument 10 under beam 40, sector 2 covers an arc which would position arm above components of the various modules where there are obstructions, sector 3 covers an arc over the right side of the rear of instrument 10 under beam 40, and sector 4 covers an arc where gripper arm 103 would hit a back wall of instrument 10. If robotic arm 100 is to be homed in the x-direction by moving the left along rail 113, gripper arm 103 must face to the right of instrument 10 with gripper arm 103 confined to a position in sector 3. Similarly, if robotic arm 100 is to be homed in the x-direction by moving the right along rail 113, gripper arm 103 must face to the left of instrument 10 with gripper arm 103 confined to a position in sector 1. Thus, before x homing is performed, instrument 10 determines what sector gripper arm 103 is in and, with an exception to be described below, moves it to either sector 1 or 3 depending on the direction in which robotic arm is homed. (In a single robot arm system, the closest side of instrument 10 may be selected for homing to home as quickly as possible. In the dual robotic arm system described below, the left arm would home to the left and the right arm would home to the right.)

The robotic controller determines which sector gripper arm is in by reading the status of sensors 212, 213 and causes gripper arm 103 to rotate into homing sector 1 or 3, if it is not there already. Depending on the theta position of robotic arm 100, the perimeter of encoder ring 211 blocks the infrared beam in neither of sensors 212, 213 when that sector is adjacent sensors so both sensors are ON in sector 4, only outer sensor 213 is ON and inner sensor 212 is OFF when sector 3 passes adjacent sensors 212, 213, both sensors are OFF in sector 2 when sector 2 is adjacent sensors 212, 213, and inner sensor 212 is ON while outer sensor 213 is OFF when sector 1 is adjacent sensors 212, 213. The absolute encoder thereby knows what sector the robotic arm is in.

Robotic controller must also insure that gripper arm 103 is in a safe area along the x-axis for the rotation of gripper arm 103 over theta into sectors 1 and 3 before homing along the x-axis is performed. The required determination is made with another absolute two-bit encoder comprising a zonal encoder bar 580 mounted in front of a portion of beam 40 (FIGS. 2 and 3B) and two optical vane-type sensors 590, 591 (FIG. 4B) mounted to a sensor mount 593 on the top of saddle platform 101. Sensor mount 593 has two tiers 595, with tier 596 elevated above tier 595 to position sensor 590 higher than sensor 591. The absolute two-bit encoder demarcates three zones along the x-axis, zones 1–3 (FIG. 3B). It is safe to move gripper arm 103 in the theta direction with the pivot point of gripper arm 103 (which is around lead screw 250) anywhere in the middle zone 2 and unsafe to move gripper arm 103 in the theta directions in zones 1 and 3 because of obstructions.

Zonal encoder bar 580 extends lengthwise across only a portion of beam 40, viz. zones 1 and 2 to minimize the length of bar 580. It is unnecessary for bar 580 to extend to zone 1 and 4. The bottom of zonal encoder bar 580 extends below the front of beam 40 a sufficient distance to pass through both sensors 590, 591 as robotic arm 100 moves in the x-direction. An elongated opening 598 is left in the zonal encoder for 580 toward the bottom of zonal encoder bar 580 across the length of zone 2 and is covered with a transparent plastic. When robotic arm 100 is in zone 1, both sensors 590, 591 are OFF because they are blocked by bar 580. When robotic arm 100 is in zone 2, lower sensor 591 passes across opening 598 and is ON while upper sensor 590 is blocked and is OFF. Bar 580 ends at the edge of zone 3 so that when robotic arm 100 is in zone 3, both lower and upper sensors 590, 591 are ON.

The precise coding of the sectors and zones defined by encoder ring 211 and zonal encoder bar 580 in combination with the sensors, i.e., which sensors must be ON or OFF to indicate a particular sector or zone, is generally unimportant as long as robotic controller has a particular code associated with each sector or zone. However, because the positioning of robotic arm 100 is critical to successful homing, the coding scheme should be a gray coding scheme in which the movement from one sector into an adjacent sector does not cause both bits for both sensors 212, 213 along theta to change. There is a similar restriction for sensors 590, 591 along the x-axis. Otherwise, a simultaneous change in both sensors would create a brief moment when both sensors in either the theta or x directions are neither ON nor OFF and could lead to an instability.

If robotic arm 100 is in zone 2 where theta movement is permitted, gripper arm 103 is rotated to sectors 1 or 3 and then x homing may be performed. X homing is also permitted if gripper arm 103 is already in sectors 1 or 3 prior to homing. If, however, robotic arm 100 is in one of zones 1 or 3 and gripper arm 103 is not in sectors 1 or 3 prior to homing, robotic controller is unable to home robotic arm 100 without manual intervention. This latter condition should not occur during normal operation of instrument 10 unless an operator has previously improperly manually moved robotic arm 100 into such a space where it is impossible to automatically home.

As described above, the theta homing mechanism also includes homing plate 214 and pin 217 (FIG. 5C).

If the absolute two bit encoders for theta and the x-axis determine that it is safe for robotic arm 100 to be homed, robotic arm 100 is homed along the x-axis by moved robotic arm 100 to the left or right until it contacts a preselected hard stop on beam 40. After robotic arm 100 has been homed against a hard stop, an incremental encoder built into x-motor 160 tracks the precise position of robotic arm 100 along the x-axis. Robotic arm 100 is then moved from the hard stop position to zone 2 for theta homing. To home as rapidly as possible, robotic arm 100 need only be moved to the edge of zone 2 closest to the hard stop against which robotic arm 100 was homed or slightly inward therefrom into zone 2. Robotic arm 100 is now homed in the theta direction by rotating robotic arm 100 in a clockwise or counterclockwise direction until robotic arm 100 no longer rotates because pin 217 in track of homing plate 214 prevents further movement. An incremental encoder built into theta motor 170 tracks any further rotation of robotic arm 100 about theta.

Grippers 104 are maintained in their closed position when not opened to grip a container and are not homed as part of the homing of robotic arm 100. If fingers 105 are holding a container at the time that power is turned off, robotic controller will be aware of this because sensor 530 on fingers 105 is ON and the operator will be alerted to remove the container.

An uninterrupted power supply ("UPS") is preferably attached to instrument 10 to allow for an orderly shut down of instrument 10, including the saving of various information and the transport of a container already carried by robotic arm 100 to its destination.

Before containers are input into instrument 10, the user identifies the particular container to instrument 10 with a bar code placed on the container and other significant information, such as, where the container is a test tube, what tests are to be performed on the sample in the test tube, or, where the container contains reagent or diluent, what reagent or diluent is in the container. The user may also enter information that identifies the height of the test tube or other container or the instrument itself may measure the height of the test tube or other container. Using this information, the robotic arm may be requested to transport a particular container, such as when an analytical module is ready to perform a test on a test tube or has completed performing the test, or when an additional reagent package is needed or is ready for disposal. The user need not enter information regarding the diameter of a test tube as that information is determined by how far grippers 104 close during the gripping process.

Software for instrument 10 is programmed into the sample handler microcontroller to provide the instructions for the order of priority in which containers will be moved. The particular programming will vary depending upon the attached modules and user preference. Also programmed into the software are the instrument-specific x-y coordinates where containers may be located for pickup or should be dropped off.

Figure 14:
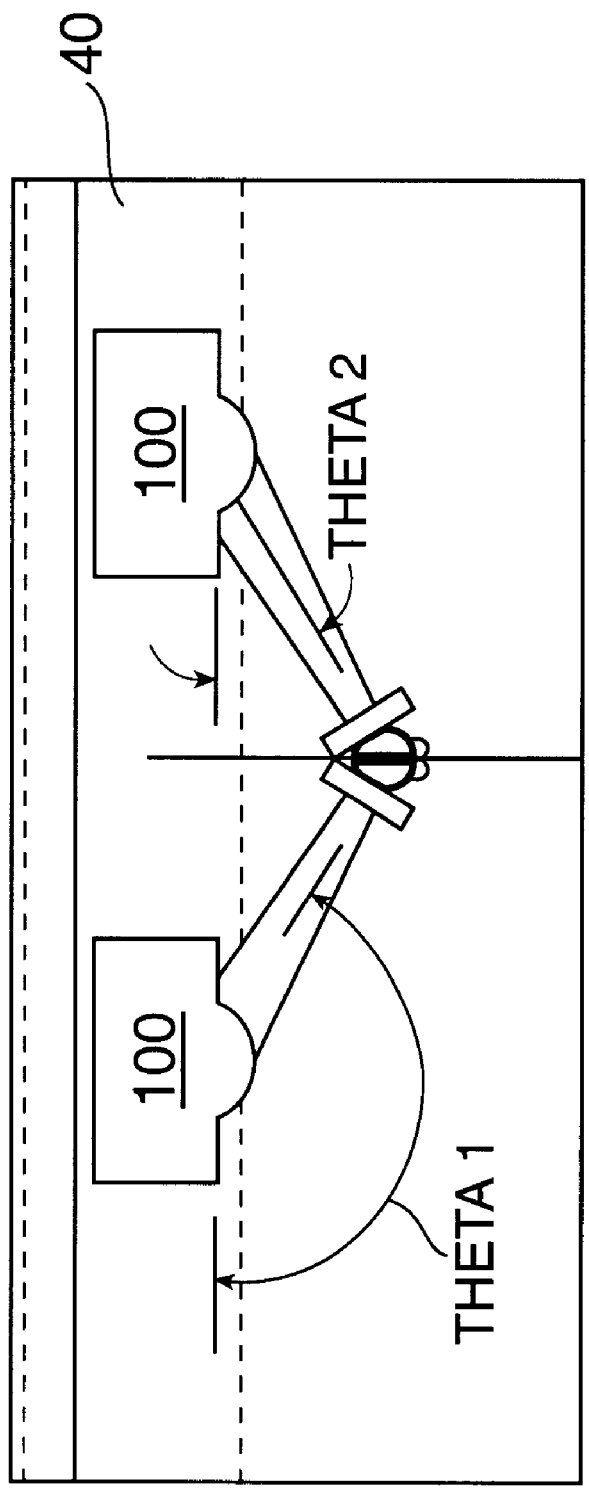
FIG. 14 is a plan view of a representation of a positional ambiguity presented by a robotic arm that may move in x and theta directions.

The software converts x-y coordinates into x and theta coordinates for moving robotic arm 100. A positional ambiguity is presented by this mapping over x, y coordinates into x and theta coordinates because the robotic arm 100 may approach some x-y coordinates from either an acute or obtuse theta angle such that saddle platform is in one of two possible positions along the x-axis. This problem is represented in FIG. 14. This ambiguity is simply resolvable by approaching the desired x-y coordinate from whichever angle enables the x-y coordinate to be reached as quickly as possible. In other areas, such as the leftmost and rightmost ends of instrument 10, there is no positional ambiguity as a specific x-y coordinate is only reachable from a single angle theta.

When a module calls for a container, robotic arm 100 moves to the location of the requested container by first moving along the x-axis (in the usual event that fingers 105 cannot reach that x-y location with a theta motion alone). After reaching the required location along the x-axis, theta motor 170 on robotic arm 100 is activated to move fingers 105 to the desired x-y position. The built-in incremental encoders in the motors track movement of x-motor 160 and theta-motor 170. Upon reaching the desired x-y position, the air-activated grippers 104 are opened and gripper arm 103 is lowered by activating z-motor 240. Optical encoder 280 for z-motor 240 tracks the travel of gripper arm 103 along z-axis.

The sample handler controller knows the height of each container before the robotic arm 100 grips the container and thereby knows the distance to which gripper arm 103 must be lowered to grip a particular container and instructs the robotic controller accordingly. To grip a test tube whose height may vary, robotic controller determines how far to lower gripper arm 103 based on the height, programmed into the robotic controller, of two types of customized test tube racks used throughout instrument 10. Thus, gripper arm 103 is lowered to position the bottom of fingers 105 approximately 3 mm above the top of a test tube rack in which the test tube is located. (The length of test tube extending beneath the bottom of fingers 105 is therefore always the same but the length of the test tube within fingers 105 differs depending on the height of the gripped test tube.) Grippers 104 then close.

When grippers 104 stop moving toward a closed position due to the resistance of the container to be gripped, encoder 540 will reflect this by not registering any movement of plate 541 on fingers 105 for 2–3 consecutive readings of encoder 540. If sensor 530 does not indicate that fingers 105 are fully closed, software in the robotic controller concludes that a container has been gripped. Linear encoder 540 tracks the distance over which fingers 105 have closed in order to determine the width of the test tube or other container and conveys that information to the controller via printed circuit board 500. If sensor 530 is activated after fingers 105 have fully closed and a container was supposed to have been gripped, the controller knows that the pickup operation was unsuccessful.

The successfully gripped container is then raised by gripper arm 103 by activating z-motor 240 in the reverse direction, moved to the desired location along the x-y axis, lowered into position, and released by fingers 105.

Figure 16:
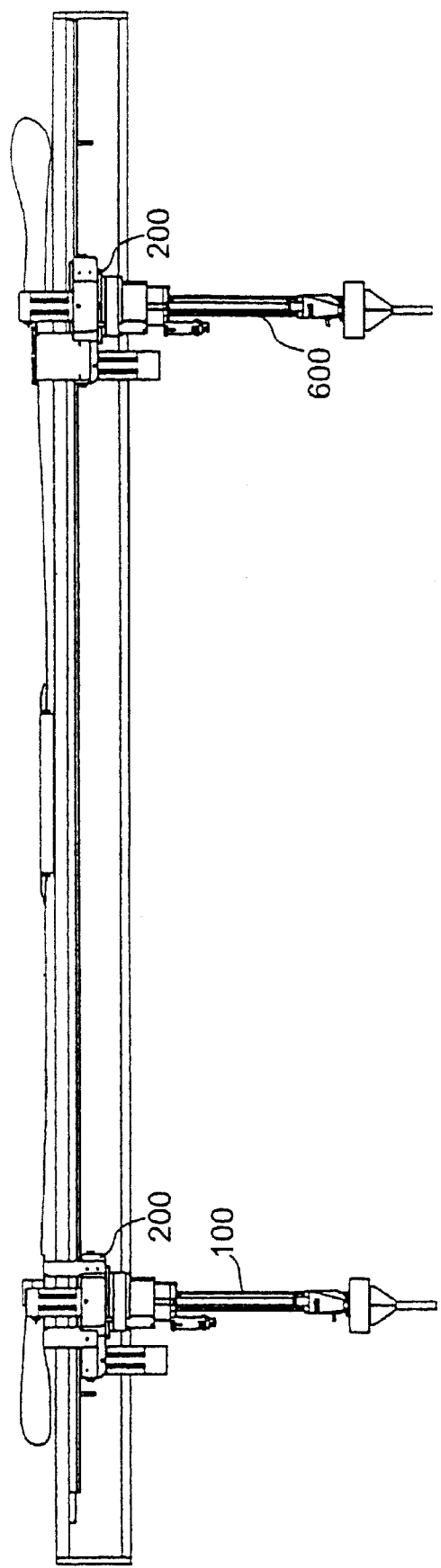
FIG. 16 is a front view of two robotic arms mounted to a beam.

A second robotic arm 600 may be added to the analytical instrument to divide the workload and improve the throughput of instrument 10. (FIG. 16) This second robotic arm 600 is particularly important where a large number of modules are included in a single instrument. The second robotic arm 600 is identical in construction to and moves along the same rail 113 and rack 112 as the first robotic arm 100. Both robotic arms 100, 600 may work in unison. A collision avoidance protocol for avoiding collisions between robotic arms 100, 600 must be incorporated into software on the sample handler controller.

One possible collision avoidance essentially works as follows (with the two robotic arms being referred to generically as robotic arm A and robotic arm B): To avoid collisions between the two robotic arms A and B, the current positions of both robotic arms are tracked. When robotic arm A receives a request to perform an operation, software in the sample handler controller determines two possible motions of robotic arm A which would cause fingers 105 to reach the same point on the x-y plane, which is a "positional ambiguity", shown in FIG. 14. The first motion would move robotic arm 100 to a first position on the x-axis and then cause robotic arm A to rotate over a first angle theta. The second motion would move robotic arm A to a second position on the x-axis and over a second angle theta to reach the same point. The software then determines what movements of robotic arm 100 are needed to get from the present position to the new position in either of the two possible motion and then estimates whether a requested move of one of the robotic arms, which we will refer to as "A", will cause that robotic arm A to collide with the other robotic arm, which we will refer to as "B". If robotic arm B will not interfere with the movement of robotic arm A in either the first or second available motions, robotic arm A is moved in the manner in which fingers 105 which will reach the desired position on instrument 10 faster. If robotic arm B is not performing a task but only one of the two possible motions will not cause a collision between the two robotic arms and the motion which is not possible is the faster of the two possible motions, robotic arm B is moved out of the way and robotic arm A moves in the manner in which fingers 105 will reach the desired position faster. But if the faster motion did not require the movement of robotic arm B, robotic arm B would not be moved. If robotic arm B is performing a task and only one of the two possible motions will not cause a collision between the two robotic arms, robotic arm A is moved in the motion that does not cause a collision. If robotic arm B is performing a task and there is no manner in which to avoid a collision if robotic arm A is moved to the desired destination, robotic arm A is not moved until robotic arm B finishes its task and moves out of the way to prevent a collision.

For purposes of homing each of robotic arms 100, 600, robotic arm 100 is homed in the x-direction by first moving its gripper arm 103 to sector 3 and then to the left along the x-axis until it hits hard stop 120 and thereafter moves to zone 2 for theta homing. Robotic arm 100 is then moved out of zone 2. Robotic arm 600 is then homed in the x-direction by first moving its gripper arm 103 to sector 1 and then to the right along the x-axis until it hits the rightmost hard stop 123 and thereafter moves to zone 2 for theta homing.

In addition to increasing the throughput, the second robotic arm 600 also adds redundancy. Should one of robotic arms 100, 600 break down, the remaining working robotic arm may perform all required operations, albeit at a reduced throughput (the actual reduction in the throughput depending on the tasks which must be performed). The malfunctioning robotic arm is disabled using the user interface to the software on instrument 10 and is then manually moved to the side of beam 40 to a park position. Hard stops 121, 122 are utilized to park the malfunctioning robotic arm and to prevent the two robotic arms from hitting one another. A malfunctioning robotic arm 100 is moved to the left side of beam 40 against hard stop 120, and hard stop 121, located on the opposite side of robotic arm 100 is rotated downward to confine robotic arm 100 to the park position between hard stops 120 and 121. A malfunctioning robotic arm 600 is moved to the right side of beam 40 against hard stop 123, and hard stop 122, located on the opposite side of robotic arm 100 is rotated downward to confine robotic arm 100 to the park position between hard stops 122 and 123.

The park positions of robotic arms 100, 600 may also be used as park positions in which routine maintenance may be performed on robotic arms 100, 600, including cleaning fingers 105 on the arms.

For easier servicing or replacement or to provide periodic lubrication, robotic arms 100, 600 may be transferred from instrument 10 to a service tool 700 shown in FIGS. 17A–17B. Service tool 700 comprises a short extension 710 to beam 40, which may be temporarily inserted into the left side of beam 40 and a rail 720. Rail 720 is mounted to the bottom of service tool 700 in the same position as rail 113 on beam 40 but there is no rack on service tool that is equivalent to rack 112. Rail 720 extends beyond beam extension 710 and passes under beam 40 to contact rail 113. In addition, rail 720 is at least as long as the combined length of the saddle platforms of the two robotic arms 100, 600. One or more alignment pins 730 on the right side of rail 720 are inserted into one or more matching holes 735 (FIG. 2) on the left side of rail 113 to assist in properly aligning rail 720 on service tool 700 with rail 113 on beam 40. Alignment pin or pins 730 may be a bullet pin, which is relatively long (on the order of several cm), in order to more easily engage the holes on rail 113. Screws 740, 741 or another securing means are inserted through holes 745 at the end of beam extension 710 and are threaded into corresponding holes on the side of beam 40 to secure the service tool 700 to beam 40.

To remove robotic arm 100, the service technician disables robotic arm 100 using the software, disconnects a connector (not shown) connecting wiring harness 300 on robotic arm 100 to electrical wiring and air lines on the instrument, and rotates upwards whichever of hard stops 120–123 is necessary to remove robotic arm 100. After installing service tool 700 on the left side of beam 40, the technician manually slides robotic arm 100 along rail 113 on beam 40 and onto rail 720 on service tool 700. Robotic arm 100 may then be removed by unscrewing the four screws connecting saddle platform 101 to bearing plate 154. Or service tool 700 with robotic arm 100 on it may be removed. Robotic arm 600 may also be similarly moved onto service tool 700 after robotic arm 100 is removed either while robotic arm 100 is on service tool 700 or after robotic arm 100 has been removed from service tool 700. Service tool 700 may have a handle 750 on the top for carrying the service tool 700 but handle 750 must be sufficiently short so the top of handle 750 does not hit plate 255, which overhangs beam 40 and service tool 700.

In order to save on processing time, the system topology including a grid of all of the potential locations to which a container may be moved is mapped out in software installed in robotic controllers before instrument 10 is first activated.

Instead of inputting test tubes into a sample handler module 20 on the instrument 10, test tubes may be input into instrument 10 through a laboratory (or "lab") automation system (not shown), such as the Lab Cell system from the Bayer Corporation. When operated in this mode, instrument 10 becomes a subsystem in the overall lab automation system. However, rather than pipetting liquid from a test tube when a rack of test tubes passes adjacent that instrument on a transport system, as in a traditional laboratory automation system, robotic arm 100 is used to remove test tubes from a transport system 800 (FIG. 1) for analysis by instrument 10 and reinsert test tubes into transport system 800 after they have been analyzed. Removing a test tube for various analyses rather than aspirating a small amount from a particular test tube with a pipette each time that test tube passes instrument 10 improves throughput as instrument 10 does not have wait for the test tube to recirculate through the transport system before aspirating a second sample for additional analysis.

Preferably, both robotic arms 100, 600 should be used when instrument 10 is used as a lab automation subsystem. Robotic arm 100 transports test tubes between a transport system 800 and a shuttle 810 on instrument 10, which may hold several test tubes at a time. A bar code reader and ultrasonic liquid level sensor (not shown) are positioned adjacent shuttle 810 to identify the test tubes in shuttle 810 and to determine if the test tubes have caps which must be removed or to read the level of liquid in the test tubes of those test tubes which do not have caps. After being read by a bar code reader and ultrasonic liquid level sensor, shuttle 810 then stops in a position where shuttle 810 is held down as test tubes are removed therefrom by either robotic arm 100 or robotic arm 600 for transport to various modules within instrument 10 other than sample handler 20.

To enable robotic arm 100 to transport test tubes from or into the lab automation system, clearance is provided on the left side of instrument 10 for robotic arm 100 to rotate outward with the end of gripper arm 103 extending beyond the left side of beam 40 and instrument 10 to reach the location of the test tube on transport system 800. To this end, the left frame of the instrument consists of two vertical posts 812, 813 with clearance between the posts for gripper arm 103 of robotic arm 100 to extend and move in the z and theta directions beyond the left side of instrument 10. A removable left side panel (not shown) may be hung over posts 812, 813 when instrument 10 is not interfaced with a lab automation system.

Lab automation systems that cannot be reached with gripper arm 103 may also interface with instrument 10 in one of two ways. As one possibility, a longer beam that extends beyond the leftmost side of instrument 10 may be substituted for the ordinary beam 40 to allow robotic arm 100 to move in the x-direction beyond the left side of instrument 10 above transport system 800 on the lab automation system. Alternatively, the gripper arm may be modified to be a two-piece gripper arm with the outer piece, to which grippers 104 mount removable, such as at point 830 (FIG. 11A) and replaceable with a longer second piece that is longer to reach farther, if necessary. A separate set of grippers 104 and fingers 105 may be mounted to the end of the extended second piece to simplify the substitution. The longer second piece may also be used on one or both robotic arms 100, 600 where instrument 10 has a module, which requires a robotic arm to have a farther reach.

A serial port on instrument 10 (not shown) for interfacing with the lab automation system is also provided One skilled in the art will recognize that modifications and variations can be made to the above-described embodiment without departing from the spirit and scope of the invention. For example, a robotic arm of the kind described, or with some features removed, may be used on an interface between a transport line and another instrument, other than the one described, to transport containers between the transport line and the other instrument.

We claim:

1. A robotic arm for an instrument having a rail, said robotic arm having a platform for coupling to said rail for movement of the robotic arm along a first axis, a gripper assembly, a first means, mounted to said platform and coupled to said gripper assembly, for moving said gripper assembly along a second axis perpendicular to said first axis, a second means, coupled to said platform, for pivoting said gripper assembly about said second axis, and an absolute encoder coupled to said gripper assembly, wherein said absolute encoder comprises a disk, having a center, a first sector and second sector, said second sector having a larger outer diameter than said first sector, and a sensor positioned adjacent said disk to detect said larger outer diameter of said second sector of said disk but not said first sector.

2. An analytical instrument comprising a rail, a robotic arm, a homing device being co-axial with said rail and defining a plurality of lateral zones, said robotic arm having a platform coupled to said rail for movement of the robotic arm through said plurality of zones along a first axis, a gripper assembly, a first means, mounted to said platform and coupled to said gripper assembly, for moving said gripper assembly along a second axis perpendicular to said first axis, and a second means, coupled to said platform, for pivoting said gripper assembly.

3. The instrument of claim 2 further comprising a beam to which said rail and said zonal homing device are mounted, and wherein said zonal homing device comprises a bar, mounted to said beam having a plurality of elongated openings therein so as to define said plurality of zones along said beam, and a sensor coupled to said platform, said bar being shaped to trigger said sensor when said platform of said robotic arm is in said first zone and not to trigger said sensor when said platform is in a second position along said first axis.

4. In an analytical instrument having a robotic arm, at least a first zone and a second zone, and a first absolute encoder for detecting said first and second zones, a method of determining whether said robotic arm may be safely homed without hitting an obstruction on said instrument comprising using said first absolute encoder to determine whether said robotic arm is in said first zone or said second zone.

5. The method of claim 4 wherein said first and second zones comprise first and second arcuate sectors, respectively, about a first axis, and said instrument further comprises a second axis, at least a third zone, in which said robotic arm may be rotated between said first and second sectors about said first axis without hitting said obstruction on said instrument, and a fourth zone, in which said robotic arm may not be rotated between said first and second sectors, said third and fourth zones extending along said second axis, and a second absolute encoder, said method further comprising defining said third and fourth zones with said second absolute encoder to determine whether said robotic arm is in said third zone or said fourth zone.

* * * * *